United States Patent
Tsygankov et al.

(10) Patent No.: US 8,143,213 B2
(45) Date of Patent: Mar. 27, 2012

(54) EFFECT OF TULA ON HIV

(75) Inventors: Alexander Tsygankov, Wyncote, PA (US); Evgeniya Smirnova, Wyncote, PA (US)

(73) Assignee: Temple University—of The Commonwealth System of Higher Education, Philadelphia, PA (US)

( * ) Notice: Subject to any disclaimer, the term of this patent is extended or adjusted under 35 U.S.C. 154(b) by 188 days.

(21) Appl. No.: 12/439,939

(22) PCT Filed: Sep. 17, 2007

(86) PCT No.: PCT/US2007/078652
§ 371 (c)(1),
(2), (4) Date: Mar. 12, 2009

(87) PCT Pub. No.: WO2008/034133
PCT Pub. Date: Mar. 20, 2008

(65) Prior Publication Data
US 2010/0160221 A1      Jun. 24, 2010

Related U.S. Application Data

(60) Provisional application No. 60/825,789, filed on Sep. 15, 2006.

(51) Int. Cl.
*A61P 31/14*      (2006.01)
*A61P 31/18*      (2006.01)
*C12N 7/00*       (2006.01)
*A61K 48/00*      (2006.01)

(52) U.S. Cl. ....... 514/3.7; 514/3.8; 514/44 R; 435/235.1

(58) Field of Classification Search .................. None
See application file for complete search history.

(56) References Cited

OTHER PUBLICATIONS

Matsuda et al., 2004, Geneseq Accession No. ADQ95863, computer printout, p. 11-14.*
Tang et al., 2002, Geneseq Accession No. ABZ11374, computer printout, pp. 5-8.*
Collingwood et al (Journal of Biological Chemistry 282:30920, 2007).*
Feshchenko et al (Oncogene 23:4690-4706, 2004).*
Torchilin (Drug Discovery Today:Technologies, vol. 5:e95-e103, 2008) (in IDS).*
Smirnova et al (Virology 372:10-23, 2008, not prior art).*
International Search Report based on PCT/US2007/078652 dated Sep. 17, 2007.
Carpino, Nick et al., Identification, cDNA Cloning, and Targeted Deletion of p70, a Novel, Ubiquitously Expressed SH3 Domain-Containing Protein, Molecular and Cellular Biology, Nov. 2002, vol. 22, Nos. 21, pp. 7491-7500.
Kowanetz, Katarzyna et al., Suppressors of T-cell Receptor Signaling Sts-1 and Sts2 Bind to Cbl and Inhibit Endocytosis of Receptor Tyrosine Kinases, The Journal of Biological Chemistry, 2004, vol. 279, No. 31, pp. 32786-32795.
Feshchenko, Elena et al., TULA: an SH3- and UBA-containing protein that binds tio c-Cbl and ubiquitin, Onocogene, 2004, vol. 23, pp. 4690-4706.
Mikhailik et al., A phosphatase activity of Sts-1 contributes to the suppression TCR signaling, Mol Cell. 27(3): 486-497 (2007).
Morgan et al., Human Gene Therapy, Annu. Rev. Biochem,.62:191-217 (1993).
Loeffler et al., Gene Transfer into Primary and Established Mammalian Cell Lines with Lipopolyamine-Coated DNA, Methods in Enzymology, vol. 17 (1993).
Tolstoshev, Gene Therapy, Concepts, Current Trials and Future Directions, Annu. Rev. Pharmacol. Toxieol. 32:573-96 (1993).
Torchilin, Intracellular delivery of protein and peptide therapeutics, 1740-6749/$ (2009).
Carpino et al., Regulation of ZAP-70 Activation and TCR Signaling by Two Related Proteins, Sts-1 and Sts-2, Immunity, 20:37-46 (2004).
Chen et al., Determination of the Substrate Specificity of Protein Tyrosine Phosphatase Tula-2 and Identification of Syk as a Tula-2 Substrate, J Biol Chem 285,31268-76 (2010).
Thomas et al., A Novel Histidine Tyrosine Phosphatase, TULA-2, Associates With Syk and Negatively Regulates GPVI Signaling in Platelets, Blood 116, 2570-8 (2010).

* cited by examiner

*Primary Examiner* — Mary E Mosher
(74) *Attorney, Agent, or Firm* — Caesar, Rivise, Bernstein, Cohen & Pokotilow, Ltd.

(57) ABSTRACT

A method of inhibiting a retrovirus production, the method includes administering a retrovirus inhibitor selected from at least one of a TULA protein, a fragment of TULA containing a UBA domain, a UBA domain of TULA, a peptide mimicking TULA, a peptide mimicking a fragment of TULA containing a UBA domain, a peptide mimicking a UBA domain of TULA, a polynucleotide encoding TULA, a polynucleotide encoding a fragment of TULA containing a UBA domain, a polynucleotide encoding a UBA domain of TULA, a polynucleotide encoding a peptide mimicking TULA, a polynucleotide encoding a peptide mimicking a fragment of TULA containing a UBA domain, a polynucleotide encoding a peptide mimicking the UBA domain of TULA, fragments thereof, muteins thereof, variants and splice variants thereof, and combinations thereof to a cell or a tissue infected by a retrovirus.

5 Claims, 13 Drawing Sheets

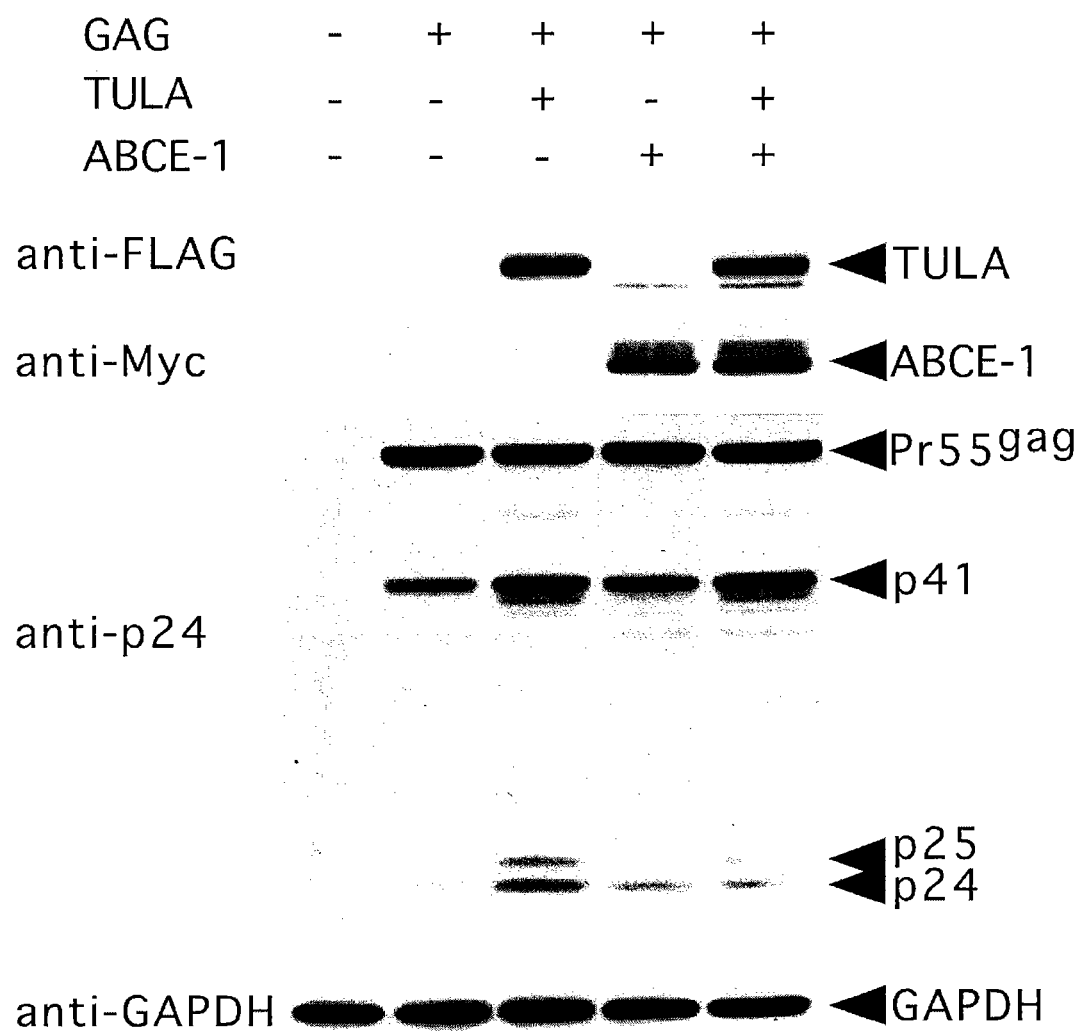

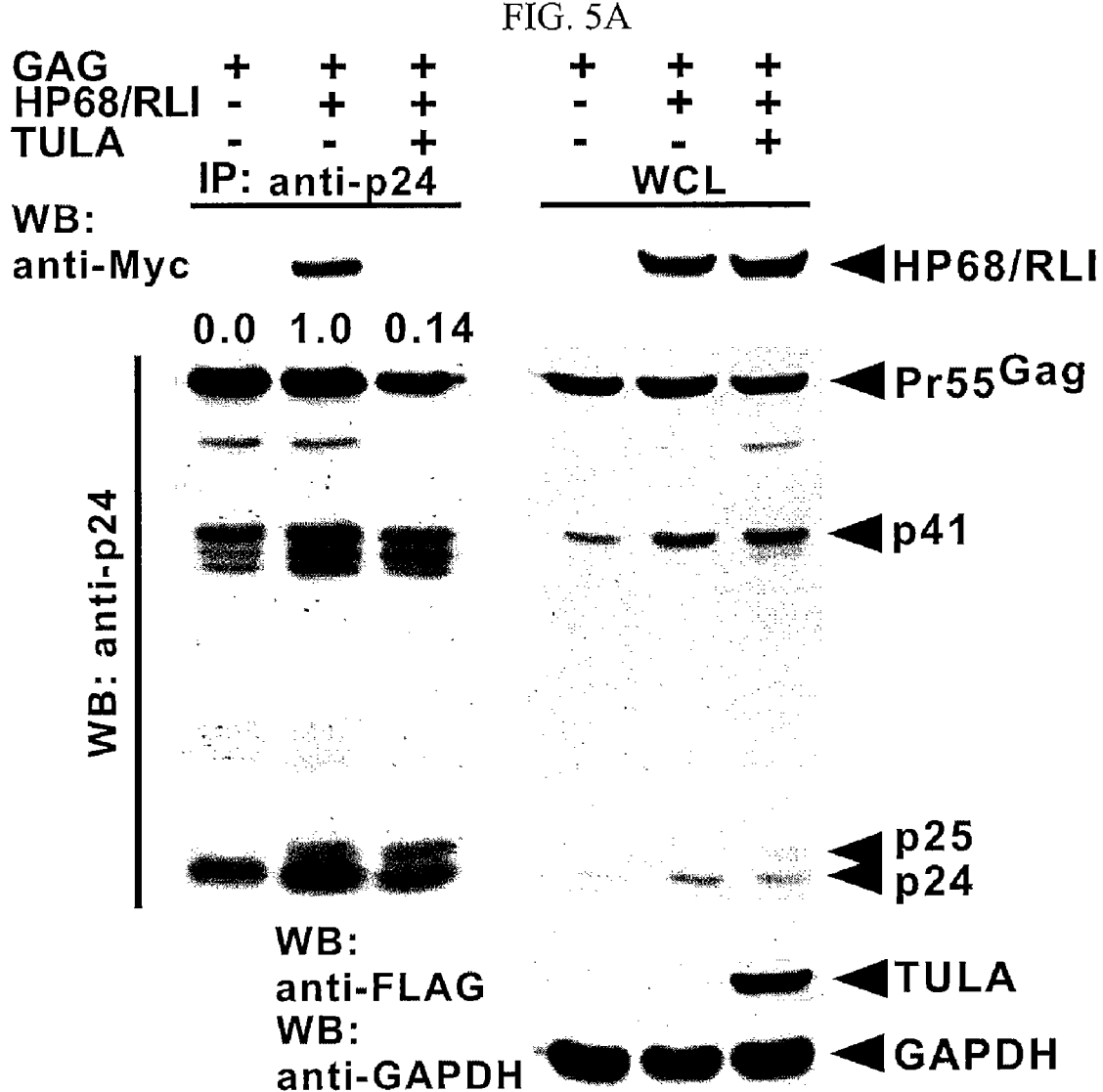

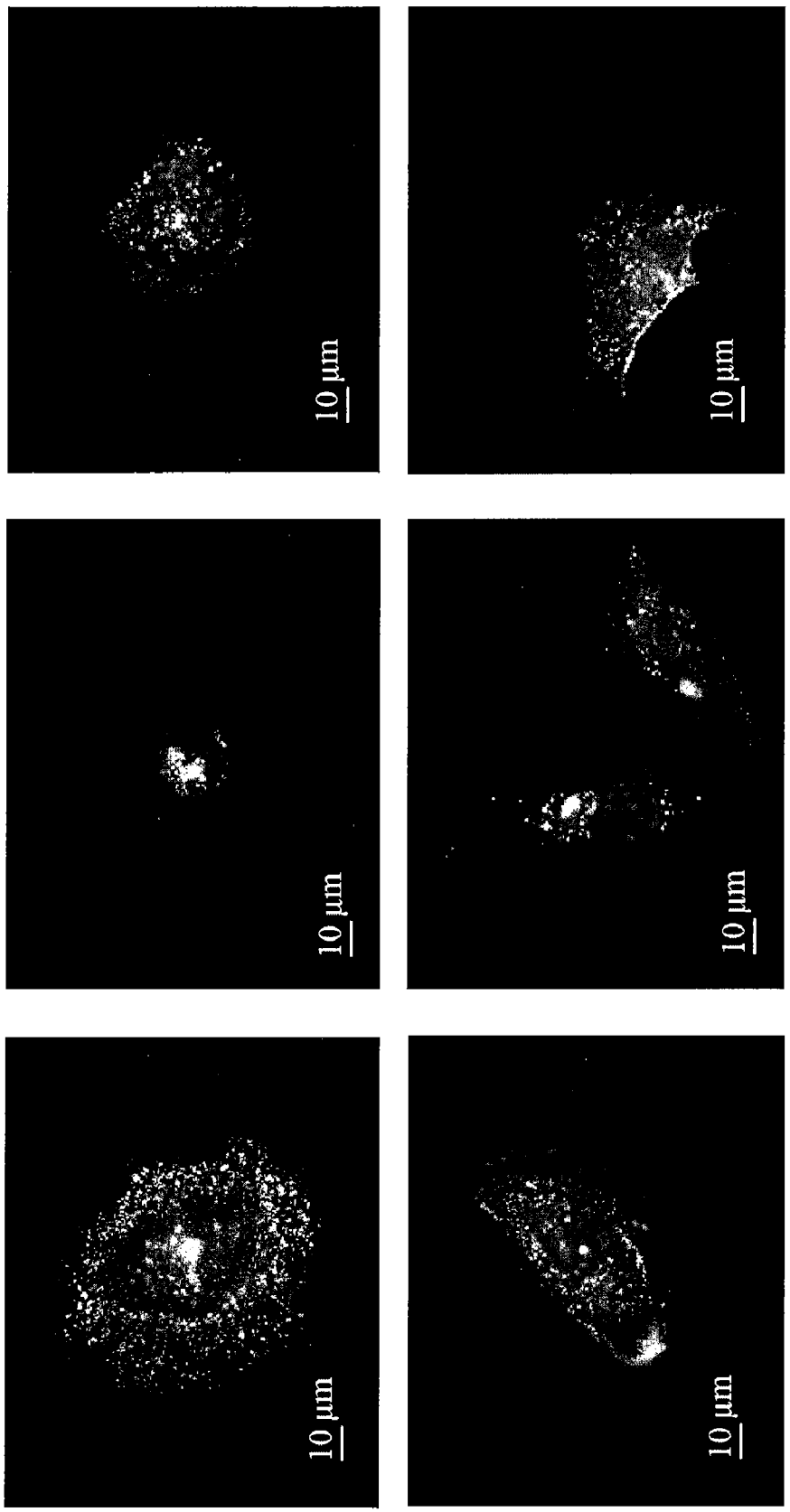

FIG. 7A

```
TULA     MAAGETQLYAKVSNKLKSRSSP------SLLEPLLAMGFPVHTALKALAATGRKTAEEAL
TULA-2   MAARE-ELYSKVTPRRNRQQRPGTIKHGSALDVLLSMGFPRARAQKALASTGGRSVQAAC
         *** *  :**:**:   :  : .*    ** *:.**:****  * ****:**..:..:..:*

TULA     AWLHDHCNDPSLDDPIPQEYALFLCPTGPLLEKLQEFWRESKRQCAKNRAHEVFPHVTLC
TULA-2   DWLFSHVGDPFLDDPLPREYVLYLRPTGPLAQKLSDFWQQSKQICGKNKAHNIFPHITLC
         .**..*  .** ****:*:**.*:* ***** :**.:**::**:  *.**:**::***:***

TULA     DFFTCEDQKVECLYEALKRAGDRLLGSFPTAVPLALHSSISYLGFFVSGSPADVIREFAM
TULA-2   QFFMCEDSKVDALGEALQTTVSRWKCKFSAPLPLELYTSSNFIGLFVKEDSAEVLKKFAA
         :**  ***.**:.* ***:   : .*    .*.:.:** *::*   .::*:**.  ...*:*:::**

TULA     TFATEASLLADCSVKPCTKQLHLTLAHKFYPHHQRTLEQLARAIPLGHSCQWTAALYSRD
TULA-2   DFAAEAASKTEVHVEPHKKQLHVTLAYHFQASHLPTLEKLAQNIDVKLGCDWVATIFSRD
         **:**:   ::  *:*  .****:***::*  .  * ***:**:  *  :  .*:*.*.:::***

TULA     MRFVHYQTLRALFQYKPQNVDELTLSPGDYIFVDPTQQDEASEGWVIGISQRTGCRGFLP
TULA-2   IRFANHETLQVIYPYTPQNDDELELVPGDFIFMSPMEQTSTSEGWIYGTSLTTGCSGLLP
         :**. ::.::**:.  .:  *.*** *** * *** :**.:.:* :* ..:****:    *  *   *** *:**

TULA     ENYTDRASESDTWVKHRMYTFSLATDLNSRKDGE-------ASSRCSGEFLPQTARSLSS
TULA-2   ENYITKADECSTWIFHGSYSILNTSSSNSLTFGDGVLERRPYEDQGLGETTPLTIICQP-
         ***. :*.*..**: *  *::   ::. **  .*:            ...:  **   *  *  ..

TULA     LQALQAT----VARKSVLVVRHGERVDQIFGKAWLQQCSTPDGKYYRPDLNFPCSLPRRS
TULA-2   MQPLRVNSQPGPQKRCLFVCRHGERMDVVFGKYWLSQCFDAKGRYIRTNLNMPHSLPQRS
         :*.*.*:..     ::.:*  ::* ***** *  :***  **.**    ..*:*  *  :**:*  ***:**

TULA     RGIKDFENDPPLSSCGIFQSRIAGDALLDSGIRISSVFASPALRCVQTAKLILEELKLEK
TULA-2   GGFRDYEKDAPITVFGCMQARLVGEALLESNTIIDHVYCSPSLRCVQTAHNILKGLQQEN
         *::*:*:*:*.*::    * :*:**:.*.*   *   *:*:.:****:.   *. *:.**:******: **: *:  *:

TULA     KIKIRVEPGIFEWTKWEAGKTTPTLMSLEELKEANFNIDTDYRPAFPLSALMPAESYQEY
TULA-2   HLKIRVEPGLFEWTKWVAGSTLPAWIPPSELAAANLSVDTTYRPHIPISKLVVSESYDTY
         :: *******:******.**.*  *: :.  .**  **::**  ***.:.:* *:  :***: *

TULA     MDRCTASMVQIVNTCPQDTGVILIVSHGSTLDSCTRPLLGLPPRECGDFAQLVRKIPSLG
TULA-2   ISRSFQVTKEIISECKSKGNNILIVAHASSLEACTCQLQGLSPQNSKDFVQMVRKIPYLG
         :.*.     :*:.   *  .  ****:*.*::**  *  *:**. **.*::. **.*:***** **

TULA     MCFCEENKEEGKWELVNPPVKTLTHGANAAFNWRNWISGN
TULA-2   FCSCEELGETGIWQLTDPPILPLTHGPTGGFNWRETLLQE
         :* ***  * * *:*.:**: .****...**** *::  : :
```

FIG. 7B

```
File1: TULA hu cDNA
Mode: Normal            1 -    1986
File2: TULA-2/STS-1 hu cDNA
Mode: Normal           34 -    1950
Matching Percentage (Total Window: 59%, Alignment Window: 59%)

1 ATGGCAGCGGGGGAGACGCAGCTCTAC-GCCAAGGTCTCCAACAAGCTCA           50
      ||||| ||| | ||| | |||| ||| || ||| || || |   | ||
   34 ATGGCTGCGAGAGAG—G-AGCTGTACAGCAAAG-TCACCC-C---C-CG           83

51 -AG-AGCCGC-AGCAGC-CCCTCG-C----TC---C-TGGA—G-C-C--          100
      || | |||| | |||| ||| || |     ||   | |||| | ||  |||
   84 GAGGAACCGCCAACAGCGCCC-CGGCACCATCAAGCATGGATCGGCGCTG          133

101 —C---CTCCTGGCCATGGGCTTCCCG-GTGCACAC-CGCGCTGAAAGCG          150
       |    ||||| |||||||| ||||| | || | ||| | |||||
  134 GACGTGCTCCTCTCCATGGGGTTCCCCAGAGC-C-CGCGCACAAAAAGCC          183

151 TTGGCAGCCACGGGGAGGAAGACG-G—CGGAGG-AGGCCT-TGGCCTGG          200
      |||||| ||||||| ||||||| | | |  ||| || | | | | ||||
  184 TTGGCATCCACGGG-AGGAAGAAGTGTTC--AGGCAG-CATGTGAC-TGG          233

201 CTGCATGATC--ATTG-CAATGACCC-TTCCCTAGACGACCCCATCCCCC          250
       | || || || | ||  |||||| |||| | || ||||||| | ||||
  234 TT--ATTCTCCCAT-GTCGGTGACCCCTTCC-TGGATGACCCCCTGCCCC          283

251 AGGAGTATGCCCTTTTCCTCTGTCCAACGGGGCCCCTGCTGGAA-A-AA-          300
      |||||| | ||| | |||| |||| || || |||||  | | | ||
  284 GGGAGTACGTCCTCTACCTCCGTCCCACCGG-CCCCT--TAGCACAGAAG          333

301 CTT-CAAGAGTTCTGG-AG-AGA-GA-GCA-AGC-GCCAGTGTGCAAAGA          350
      ||| |   || || |||| || |  || |||| |  | || ||  || ||
  334 CTTTCC-GACTTTTGGCAGCAGTCGAAGCAGATCTGC--G-G-G-AA-GA          383

351 ACAGAG-CTCATGAGGTCTTCCCACACGTGACACTCTGTGACTTCTTCAC          400
      ||| || | ||| | ||||||| ||| | ||||||| | | |||| |
  384 ACA-AGGCACACAACATCTTCCCCCACATCACACTCTGCCAGTTCTTTAT          433

401 GTGTGAAGACCAG-AAGGTGGAATGCCTGTACGAGGCGCTGAAGAGAGCT          450
      ||| || ||| || ||||||||| ||||  |  | || | ||||   ||
  434 GTGCGAGGAC-AGCAAGGTGGA-TGCCC-T--G-GG-G--GAAGCC--CT          483

451 GGAGACAGGCTCCTGGGCTCCTTCCCCACGGCCGTGCCTCTGGCTCTCCA          500
      | |||| | || || ||       | | | | || | | | ||||    |
  484 GCAGAC---CAC--GG--TC-------A-GTC-G--C-T--GGAA----A          533

501 CTCCTCCATCAGCTACCTCGGCTTCTTCGTCAGTGGCAGCCCCGCAGACG          550
       | | | | || | | ||||| | ||| || || ||| ||| || ||
  534 -TG-T--A--AGTT-C-TCGGCC-C--CG-C--TG-C--CCCTG--GA-G          583

551 TCATCCGGGAATTCGCCATGACCTTCGCCACGGAAGCATCTCTCTTAGCA          600
       |||     |    |||| |||| |||| |||| || | |||| |   |
  584 -C-TC------T-----AT-ACGT-CGTC-C--AA-C-T-TCA-T---C-          633
```

FIG. 7B (con't)

```
601  GGCACTTCCGTTTCCCGCTTCTGGATTTTCAGCCAGGTGCCTGGACATGG    650
     ||| || |  ||| || | |||  ||| || ||| ||  ||
634  GGC-CT-C--TTT---G-TAAAGGA-----AGACAG-TGC--GGA---GG    683

651  CCCT-AACCTGAGGCTGAGCAATTTAACTAGAGCCTCCTTCG-TG-AGCC    700
     ||| ||   || ||| ||  ||    || ||| | ||  || ||| ||
684  TCCTCAA---GAAGTTT-GC--TG---CT-GA-C-T--TT-GCTGCAG--   733

701  A--CTACATCCTTCAAAA---ATACTGC-TCCGTG-AAGCCTTGCACCA-   750
     |  || |||||    ||||    | ||| | ||| || || || || |
734  AGGCTGCATCC---AAAACCGA-AGTGCAT--GTGGAA-CCT--CATAAG   783

751  AA-CAGCTGCATCTGACCTTGGC---CCACAAGTTCTAC-CC--CCACC-   800
     || ||||||  ||| ||||||  ||||    ||||   ||| |  || |||||
784  AAGCAGCTACATGTGACCCTGGCTTACCAC---TTCCAAGCCAGCCACCT   833

801  ACCAGAGGACGCTGGAGCAGCTGGCC-AGAGCCATCCCCCTGG-GCCACA    850
     |||  |   | || ||| | |||||| ||| ||   || |||  |
834  ACCC-AC--C-CTAGAGAAACTGGCCCAGAAC-AT-----TGACGTCA-A   883

851  GCT-GCCAGTG-GACCGCA-G-C-ACTC-TACTC-C-CGAGACATGCGCT    900
     ||| |   ||| ||| |   | | | |  | || | || || || || ||
884  GCTAGG--GTGTGACTGGGTGGCTAC-CATATTTCTCGGGATATCCGAT    933

901  TTGTGCACTACCAGACCCTGAGAGCCCTATTCCAG-T-A-C-A-----A-   950
     ||| |  || |   || ||||| |     ||| ||| | || | ||||   |
934  TTG--C--TA--A--CCATGAGA-C---ATTACAGGTCATCTACCCTAT   983
                                   ----------------------

951  ACCCCAGAACGTG--GATGAGCTG-ACGCTAAGTCCT-GGTGACTACATC  1000
     |||||| || || |||||||||| | ||| ||||  || |||| ||||
984  ACCCCACAAAATGACGATGAGCTGGA-GCTG-GTCCCCGGGGACTTCATC  1033
     -------------------------------------

1001 TT--TGTGGACCCCAC-GCAGCAGGACGAAGC-C-AGCGAGGGCTGGGTG  1050
     ||  |||  | |||| |||||| ||| ||  | |||||||| |||
1034 TTCATGT---CTCCAATGGAGCAG-ACCA-GCACCAGCGAGGGTTGGATC  1083
     -------------------

1051 -ATTGGGA--TC-TCACAGCGGACGGGCTGC-CGGGGCTTCCTGCCGGA-  1100
     |||| |   ||  |  | |  || |||||| | || || |||||| ||
1084 TAT-GGCACGTCCTTA-ACC--ACCGGCTGCTCTGGACT-CCTGCCTGAG  1133
     -------------------------------------------

1101 AA--AC-T-AC-ACGGATCGA-GCCAGTG-AGTCTGACACGTGGGTGAAG  1150
     ||  || | || || |  ||| ||| | |  | ||||  || ||  |  ||
1134 AATTACATTACCAAGGCT-GATGA-A-TGCAG-C--AC-C-TGGAT-ATT  1183
     --------

1151 CACA-GGATGTAC--ACCTTCAGTCT-AGCACA--G--A-CCTGAACTC   1200
     ||  || |    |   ||||  ||| |   |||  |    ||  | |||||
1184 T-CATGG-T-T-CTTA--TTCAATCTTAAATACATCGTCATCC--AACTC  1233

1201 -C--A-GAAAGG--ATGGTG-A----AGCCAG-CAGC---A-GATG-C-A  1250
      |  |    ||  || |||| |          ||  || || || |   |||| | |
1234 TCTCACGTTTGGGGATGGAGTATTGGAG--AGGCGGCCTTATGAGGACCA  1283

1251 G---C--GGGGA-AT---T--TCTTCC-A-CAAACGGCAAGG--AGT-CT  1300
     |    |   |||||| |      ||||| | || ||||| ||  || | |
1284 GGGGCTCGGGGAGACGACTCCTCTTACTATCAT-CTGCCAGCCCA-TGC-  1333
```

FIG. 7B (con't)

```
1301 TAGCAGCTTACAGG-C-CTTGC-AGGCTACCGTTGCA---AGGAAGAGC       1350
     ||| ||| |  || |  || || |  ||| ||    || |||   |
1334 -AGCCGCTGAG-GGTCAACA-GCCAG-C--CCG--GCCCCCAG-AAG--C       1383

1351 G-TGC-TGGT-G-GT-TCGCCACGGGGAGACAG-TGGATCA-GATCTTCG       1400
     | ||| |  | | || ||| || || ||||| | ||||| |    | |||
1384 GATGCCTTTTGTGTGTCGGCATGGTGAGAG-GATGGATGTTG-TGTTTG      1433

1401 GGAAGGCA-TGGCTG-CAGCAATGCTCC-ACT-CCTGATGG--GAAATAC      1450
     |||||   | ||||||| || ||||| | | || | ||  |       |||
1434 GGAAGT-ACTGGCTGTCC-CAGTGCTTCGA-TGCCAAA-GGCCGC--TAC    1483

1451 -TACAGG-CCAGACCTGAATTTCCCCTGCA--GTCTGCCA-AGACGGAGT     1500
     ||| |   ||| ||||||||  | ||  || || | || || ||||||
1484 ATAC-GCACCA-ACCTGAACATGCC-T-CATAGTTTACCTCAG-CGGAGT     1533

1501 CGTGGGATCAAAGACTTT-GA-AAACGATCC-CCCATTATCATCGTGT--     1550
     ||||  ||  ||| ||   ||  ||| ||| | |||||  |  | ||||
1534 GGTGGTTTCCGAGA-TTACGAGAAA-GATGCTCCCATCA-C-T-GTGTTT    1583

1551 GGCATTTTCCAGTCCA-G-AATTG-C-AG-GGG--ACGCGCT-ACT-G-G     1600
     || ||   |   | |||| |  | | ||| | |  ||   | || || | |
1584 GG-ATG--C-A-TGCAAGCAA--GACTAGTGGGTGAAGC-CTTATTAGAG     1633

1601 A-CAGTGGTATCAGAATCAGCTC-TGTGT-TTGCCTCCCCAG-CCCTCCG     1650
     | |||        | |||   ||| || ||| |  ||||| ||||| ||
1634 AGCAAT---ACCATTATC-GATCATGTCTATTGC-TCCCC-GTCCCTTCG    1683

1651 CTGTGTGCAGACGGC-CA-AACTCATCCTGGAAGAACT-CAAACTGGAGA     1700
     ||| || ||||| || || ||  |  || ||| |||| |   |||  |||
1684 CTGCGTTCAGACTGCACACAA-T-ATCTTGAAAGGTTTACAA-CA--AGA    1733

1701 AAAAAA-TC-AAGATACGAGTGGAACCTGGAATCTTTGAATGGACAAAAT     1750
     |||    || ||  |||| ||  ||  || ||| |  ||||||||||||
1734 AAATCACTTGAAGATCCGTGTAGAGCCCGGCTTATTTGAGTGGACAAAAT    1783

1751 GGGAAGCTGGCAAAACCACCCCA--ACCCT-CATG-AG-CCTGGA--AGA     1800
     |||  ||||| |    | ||     |  ||||  ||  ||| ||   |||
1784 GGGTTGCTGGGAG--C-AC---ATTACC-TGCATGGATACCTCCATCAGA    1833

1801 G----CTG-A---AA---GAG-GCAAATT--T-CAACATTGACACTGAT-    1850
     |   ||| |   ||   ||| || |  | | || | |||| |||   ||
1834 GTTAGCTGCAGCCAACCTGAGTG----TTGATACAACCT--ACA--GACC    1883

1851 T-ACAGGCC---C-GCG--TT--TCCCCTGTC-C-GC--CCTCATGC--C    1900
     |  || ||    | | |  ||  || | ||    |||  || | ||   |
1884 TCACATTCCAATCAGCAAATTAGT----TGTTTCAGAATCCT-ATGATAC    1933

1901 GGC---C-G-AGA-GCTACCAGGAGTA-CATG-GACAGGTGCACGGCGAG    1950
     || || | | | |  |||| ||||||    |
1934 TTATATCAGTAGAAGTTTCCA--AGTAACAAAAGAAA--TA-AT----A-    1983

1951 CATGGTGCAAATCGTCAACACCTGTCCACAGGACACGGGTGTCATCCTAA    2000
     | || || ||  | |||| |   |||||     |   ||||||||||| |
1984 -A-G-TG-AA-T-GTAAA-A---GTA-A-AGGAAA----TAACATCCTGA    2033
```

FIG. 7B (con't)

```
2001 TTGTGAGTC-ACGG--CT-CCACTCTGGACTCCTGCACGCGGCCA-CTGC      2050
     |||||  |  |||    || || || ||  |  | || || | |||| ||
2034 TTGTG-GCCCACGCATCTTCC-CT-TGAAG-CGTGTAC-CTGCCAACT--      2083

2051 TC-GGGC-TGCCGCCCCGGGAA-TGTGGGGATTTTGCCCAACTCGTGAGA      2100
     || ||||  || |  ||  | ||  |   ||| ||    |  | ||  ||
2084 TCAGGGCCTGTCACCTCAG-AACTCCAAGGACTTCGTACAAATGGTCCGA      2133

2101 AAGATCCC-T-TCCCTGGGCATGT-GCTTC-TGTGAAGAAAATAAAGAGG      2150
     ||||||||  |   |||| || |    | |  |||||||||||  | |||
2134 AAGATCCCATATC--TGGG-ATTTG-TTCCTGTGAAGAAT-TAG-GAGA       2183

2151 AA--GGAAAATGGGAGTTGGT-GAACCCACCGGTGAAGAC--CCTG--AC      2200
     ||   ||||  |||| || ||   || || |||    ||   |||   ||
2184 AACTGGAATATGGCAGCTGACAGATCC-ACC----AATCCTTCCTCTTAC      2233

2201 CCACGGGGCGAAC-GCAG-CATTTAACTGGAG-GA-AC-TGGATCTCAGG      2250
     ||| ||  | ||| |  |  |  || |||||||| || | |   ||| |
2234 CCATGGACC-AACTGGGGGC-TTCAACTGGAGAGACCTTGCT-TCAAG        2283

2251 CAACTGA.........................................      2300
       || | |
2284 -AA-TAA.........................................      2333
```

EFFECT OF TULA ON HIV

This application is a U.S. national stage of international application PCT/US07/78652, filed Sep. 17, 2007, which claims the benefit of U.S. provisional application No. 60/825,789, filed Sep. 15, 2006.

STATEMENT REGARDING FEDERALLY SPONSORED RESEARCH OR DEVELOPMENT

This invention was made with government support under National Cancer Institute Grant No. CA78499 awarded by the National Cancer Institute. The government has certain rights in the invention.

BACKGROUND OF THE INVENTION

1. Field of Invention

This invention relates to host cell proteins involved in retrovirus replication. More specifically, the invention relates to host cell proteins involved in human immunodeficiency virus (HIV-1) replication.

2. Description of Related Art

Retroviral agents have been implicated in a number of diseases, including cancer, autoimmune disease and AIDS. Human immunodeficiency virus (HIV) infection causes chronic progressive depletion of CD4$^+$ T lymphocytes (CD4$^+$ cells) and infection of macrophages, resulting in acquired immune deficiency syndrome.

Human immunodeficiency virus type 1 (HIV-1), a retrovirus, is the etiologic cause of AIDS. The HIV-1 envelope glycoprotein, gp120, specifically binds to the CD4 receptor on T lymphocytes and on monocytes and macrophages. Although infection of T lymphocytes requires cellular proliferation and DNA synthesis, productive infection of monocytes can occur independently of cellular DNA synthesis (Weinberg, J. B., et al., (1991) J. Exp. Med. 174:1477-82). When HIV-1 infects activated CD4$^+$ lymphocytes, it is lethal, but infected monocytes are relatively resistant to destruction by the virus. Consequently, these cells, once infected with HIV-1, serve as long-lived reservoirs of the virus. Not only are these cells a source of replicating virus, but their virally-mediated dysfunction may contribute to increased susceptibility to opportunistic infections that are the hallmark of AIDS.

One of the current directions in anti-HIV-1 drug development focuses on the invariant host cell proteins involved in HIV-1 replication. Recently, a number of host cell proteins have been found to be necessary for HIV-1 replication and infectivity. In contrast, little is known about the proteins participating in the cellular defense against HIV-1 infection.

Feshchenko et al. identified TULA, a lymphoid SH3- and UBA domain-containing protein, which binds to ubiquitin and the ubiquitin-protein ligase c-Cbl (TULA: on SH3- and UBA-containing protein that binds to c-Cbl and ubiquitin. Oncogene 23, 4690-4706 (2004)). It was shown that TULA counteracts c-Cbl-dependent downregulation of protein tyrosine kinases (PTKs) and PTK-mediated signaling in a UBA-dependent fashion.

The gene encoding for TULA, which was termed UBASH3A, was examined by Wattenhofer et al. for possible involvement in autosomal recessive deafness; the authors concluded that UBASH3A plays no role in this disease [1]. The protein product of UBASH3A was not isolated or analyzed in this study, but the prediction based on the gene sequence showed that this protein possesses an SH3 and a UBA domain and a region of homology with some human, worm and fly proteins referred to as HCD (FIG. 1).

Feshchenko et al. identified the protein product of UBASH3A in the course of co-purification of c-Cbl with c-Cbl-associated proteins from the JMC-D3 clone of the human T-cell line Jurkat [2]. The ability of this protein to bind to c-Cbl via the interactions of its SH3 domain and the proline-rich region of c-Cbl was confirmed using co-immunoprecipitation and in vitro "pull-down" assays. Using Northern blotting, RT-PCR and Western blotting, expression of TULA in various cell lines and tissues were analyzed. It was demonstrated that TULA is preferentially expressed in lymphoid cells. Feshchenko et al. also showed that this protein binds well to ubiquitin via its UBA domain. Considering this finding and the predominant expression of this protein in T lymphocytes and other cells of lymphoid lineage, this protein was termed T-cell ubiquitin ligand (TULA). It was further demonstrated that TULA inhibits c-Cbl-dependent downregulation of protein tyrosine kinases (PTKs) [2].

Two other groups have published results related to TULA. Carpino et al. identified TULA, which they termed Sts-2, independently [3]. The results obtained by this group are similar to those described in [2] with regard to TULA expression, but are different with regard to TULA's interactions with other proteins. Carpino et al. failed to show TULA's binding to c-Cbl or stabilization of PTKs. A more recent study of TULA (Sts-2) by Kowanetz et al. [4] has corroborated the data described in [2] on c-Cbl binding and PTK stabilization.

The second protein of the TULA family (NP_116262, BAC11468), referred to as TULA-2 herein, is expressed ubiquitously [3-5]. This protein has been identified by Carpino et al. [5] and characterized by Carpino et al. [3] and Kowanetz et al. [4]. TULA-2 is similar to TULA in its ability to bind to c-Cbl and stabilize PTKs [4].

The above discussed studies do not describe the effect of TULA on HIV-1 biogenesis.

Studies of negative regulators of HIV-1 biogenesis and infectivity and were reported by Shindo et al., 2003 [6]; Mangeat et al., 2003 [7]; Zhang et al., 2003 [29]; Yap et al. [9], 2004; Carlson et al., 2004 [11]. However, none of these references characterize TULA proteins as regulators of HIV-1 biogenesis.

Several proteins have been shown to function as parts of the intracellular defense against HIV-1 infection, of which APOBEC proteins provide the best-studied example [6, 7]. APOBEC proteins are cytidine deaminases that can hypermutate nascent reverse transcripts, thus inhibiting the replication of HIV-1. However, recent findings suggest that the anti-HIV-1 effect of APOBEC proteins correlates with their ability to prevent the accumulation of reverse transcripts and not with the induction of hypermutation [8]. TRIM5α is another intracellular anti-HIV factor, which acts by promoting rapid, premature disassembly of retroviral capsids [9, 10]. OKT18, another antiviral factor, exerts its anti-HIV activity through suppression of HIV-1 transcription [11]. None of these factors can effectively suppress HIV-1 infection, since HIV-1 evades and actively counters their effects. For example, the effect of APOBEC is countered by the viral protein Vif [6, 7].

Based on the existing knowledge about cellular factors restricting HIV-1 infection, neither of these factors is related to TULA and none of their effects recapitulates the anti-HIV effect of TULA. Therefore, TULA represents a novel anti-HIV factor as discovered by the inventors.

Thus, despite the foregoing developments, there is a need in the art for cellular proteins working as natural barriers to retroviral infection and specifically to HIV-1 infection.

All references cited herein are incorporated herein by reference in their entireties.

BRIEF SUMMARY OF THE INVENTION

The present invention provides novel methods for treating retroviral infections of mammalian cells, particularly, treating infections with human immunodeficiency virus (HIV) and associated diseases, including acquired immune deficiency syndrome (AIDS).

Inventors discovered that TULA is associated with HP68/RLI, a host factor of HIV-1 biogenesis, which exerts its effect on HIV-1 particle maturation through its interaction with HIV-1 Gag. Using overexpression and RNAi-mediated knockdown, inventors demonstrated that TULA and its homologue TULA-2 inhibit HIV-1 biogenesis at the level of viral particle production.

Inventors found that the negative effect of TULA proteins is caused neither by altering expression of HP68/RLI or HIV-1 Gag nor by the exclusion of HP68/RLI from its complex with Gag.

Several host cell proteins have been found to be necessary for HIV-1 replication and infectivity. In contrast, little is known about proteins participating in the cellular defense against HIV-1 infection. Discoveries in this area may produce a new generation of anti-HIV-1 drugs that harness the effects of natural anti-HIV defense proteins. This approach has a major advantage over the strategies focused on the viral proteins, because it is likely to eliminate the problem of the high mutation rate of HIV-1 that allows HIV-1 to escape recognition either by host immune responses or by drugs inhibiting viral reverse transcriptase or protease.

Thus, in one aspect, the invention is a method of inhibiting a retrovirus production, the method comprising administering a retrovirus inhibitor selected from the group consisting of at least one of a TULA protein, a fragment of a TULA protein containing a UBA domain, a UBA domain of a TULA protein, a peptide mimicking a TULA protein, a peptide mimicking a fragment of a TULA protein containing a UBA domain, a peptide mimicking a UBA domain of a TULA protein, a polynucleotide encoding a TULA protein, a polynucleotide encoding a fragment of a TULA protein containing a UBA domain, a polynucleotide encoding a UBA domain of a TULA protein, a polynucleotide encoding a peptide mimicking a TULA protein, a polynucleotide encoding a peptide mimicking a fragment of a TULA protein containing a UBA domain, a polynucleotide encoding a peptide mimicking the UBA domain of TULA protein, fragments thereof, muteins thereof, variants and splice variants thereof, and combinations thereof to a cell or a tissue infected by a retrovirus.

In certain embodiments of the method, the retrovirus inhibitor is encoded by at least one of SEQ ID NO: 1, SEQ ID NO: 3, SEQ ID NO: 5, SEQ ID NO: 7, fragments thereof, muteins thereof, variants and splice variants thereof, and combinations thereof.

In certain embodiments of the method, the retrovirus inhibitor is at least one of SEQ ID NO: 2, SEQ ID NO: 4, SEQ ID NO: 6, SEQ ID NO: 8, SEQ ID NO: 19 fragments thereof, muteins thereof, variants and splice variants thereof, and combinations thereof.

In certain embodiments of the method, said administering is achieved by expressing at least one of a retrovirus inhibitor selected from the group consisting of at least one of a TULA protein, a fragment of TULA containing a UBA domain, a UBA domain of a TULA protein, a peptide mimicking TULA, a peptide mimicking the fragment of a TULA protein containing a UBA domain, a peptide mimicking the UBA domain of TULA protein, fragments thereof, muteins thereof, variants and splice variants thereof, and combinations thereof in the cell.

In certain embodiments of the method, the retrovirus production is HIV-1 production.

In another aspect, the invention is a kit for inhibiting production of a retrovirus in a cell or a tissue infected by a retrovirus, the kit comprising (a) a retrovirus inhibitor selected from the group consisting of at least one of a TULA protein, a fragment of a TULA protein containing a UBA domain, a UBA domain of a TULA protein, a peptide mimicking a TULA protein, a peptide mimicking a fragment of a TULA protein containing a UBA domain, a peptide mimicking a UBA domain of a TULA protein, a polynucleotide encoding a TULA protein, a polynucleotide encoding a fragment of a TULA protein containing a UBA domain, a polynucleotide encoding a UBA domain of a TULA protein, a polynucleotide encoding a peptide mimicking a TULA protein, a polynucleotide encoding a peptide mimicking a fragment of a TULA protein containing a UBA domain, a polynucleotide encoding a peptide mimicking the UBA domain of TULA protein, fragments thereof, muteins thereof, variants and splice variants thereof, and combinations thereof; and (b) instructions for administering the retrovirus inhibitor.

In certain embodiments of the kit, the retrovirus inhibitor is encoded by at least one of SEQ ID NO: 1, SEQ ID NO: 3, SEQ ID NO: 5, SEQ ID NO: 7, fragments thereof, muteins thereof, variants and splice variants thereof, and combinations thereof.

In certain embodiments of the kit, the retrovirus inhibitor is at least one of SEQ ID NO: 2, SEQ ID NO: 4, SEQ ID NO: 6, SEQ ID NO: 8, SEQ ID NO: 19 fragments thereof, muteins thereof, variants and splice variants thereof, and combinations thereof.

In certain embodiments, the kit further comprises the cell or the tissue infected by a retrovirus. In certain embodiments, the retrovirus is HIV-1.

In yet another aspect, the invention is an antigenic fragment of an isolated peptide sequence, wherein the antigenic fragment is from a peptide selected from the group consisting of SEQ ID NO: 2, SEQ ID NO:4, SEQ ID NO:6, SEQ ID NO:8, SEQ ID NO: 19 fragments thereof, muteins thereof, variants and splice variants thereof, and combinations thereof. In certain embodiments, the antigenic fragment inhibits maturation of HIV-1.

In yet another aspect, the invention is an antigenic fragment of an isolated peptide sequence encoded by a polynucleotide selected from the group consisting of SEQ ID NO: 1, SEQ ID NO:3, SEQ ID NO:5, SEQ ID NO:7, fragments thereof, muteins thereof, variants and splice variants thereof, and combinations thereof. In certain embodiments, the antigenic fragment inhibits maturation of HIV-1.

In yet another aspect, the invention is a substantially purified polypeptide selected from the group consisting of SEQ ID NO: 2, SEQ ID NO:4, SEQ ID NO:6, SEQ ID NO:8, SEQ ID NO: 19 fragments thereof, muteins thereof, variants and splice variants thereof, and combinations thereof.

In yet another aspect, the invention is a host cell comprising a retrovirus inhibitor selected from the group consisting of at least one of a TULA protein, a fragment of a TULA protein containing a UBA domain, a UBA domain of a TULA protein, a peptide mimicking a TULA protein, a peptide mimicking a fragment of a TULA protein containing a UBA domain, a peptide mimicking a UBA domain of a TULA protein, SEQ ID NO: 2, SEQ ID NO: 4, SEQ ID NO: 6, SEQ ID NO: 8, SEQ ID NO: 19, fragments thereof, muteins thereof, variants and splice variants thereof, and combinations thereof, wherein the retrovirus inhibitor modulates retrovirus production.

In certain embodiments, the host cell is a member selected from the group consisting of eukaryotic cells and prokaryotic cells.

In yet another aspect, the invention is a host cell line stably transfected with a TULA protein, a fragment of a TULA protein containing a UBA domain, a UBA domain of a TULA protein, a peptide mimicking a TULA protein, a peptide mimicking a fragment of a TULA protein containing a UBA domain, a peptide mimicking a UBA domain of a TULA protein, SEQ ID NO: 2, SEQ ID NO: 4, SEQ ID NO: 6, SEQ ID NO: 8, SEQ ID NO: 19, fragments thereof, muteins thereof, variants and splice variants thereof, and combinations thereof.

In yet another aspect, the invention is a method of treating a disorder selected from the group consisting of viral infections, HIV infection, AIDS, autoimmune disease, and cancer comprising administering to said subject a therapeutically effective amount of composition comprising (i) a first retrovirus inhibitor selected from the group consisting of at least one of a TULA protein, a fragment of a TULA protein containing a UBA domain, a UBA domain of a TULA protein, a peptide mimicking a TULA protein, a peptide mimicking a fragment of a TULA protein containing a UBA domain, a peptide mimicking a UBA domain of a TULA protein, a polynucleotide encoding a TULA protein, a polynucleotide encoding a fragment of a TULA protein containing a UBA domain, a polynucleotide encoding a UBA domain of a TULA protein, a polynucleotide encoding a peptide mimicking a TULA protein, a polynucleotide encoding a peptide mimicking a fragment of a TULA protein containing a UBA domain, a polynucleotide encoding a peptide mimicking the UBA domain of TULA protein, fragments thereof, muteins thereof, variants and splice variants thereof, and combinations thereof; and (ii) a pharmaceutically acceptable carrier.

In certain embodiments, the composition further comprises a second retrovirus inhibitor.

In yet another aspect, the invention is a method of identifying a fragment of a TULA protein having antiretroviral activity for the modulating a disorder selected from the group consisting of viral infections, HIV infection, autoimmune disease, and cancer, the method comprising:

(a) providing a cell infected with a retrovirus;
(b) providing a test agent comprising the fragment of the TULA protein;
(d) combining the cell infected with a retrovirus with the test agent;
(e) measuring retrovirus production in the presence of the test agent;
(f) measuring retrovirus production in a control sample having no test agent; and
(g) comparing retrovirus production in the control sample with retrovirus production in the test sample to identify the fragment of the TULA protein having antiretroviral activity which modulates the disorder selected from the group consisting of viral infections, HIV infection, autoimmune disease, and cancer.

BRIEF DESCRIPTION OF SEVERAL VIEWS OF THE DRAWINGS

The invention will be described in conjunction with the following drawings in which like reference numerals designate like elements and wherein:

FIG. 2A is a bar graph of percentages of infected Jurkat cells. Supernatants were harvested, filtered and 10μ-aliquots were used to transduce $2 \times 10^5$ Jurkat cells in a total volume of 500 μl. Percentage of infected Jurkat cells 48 hrs post-transduction is plotted as mean+/−SD (measurements were carried out in triplicates; vector control=100%). The results of a representative experiment of five independent experiments are shown.

FIG. 2B is a picture of a Western blot, wherein whole cell lysates (WCL) of virus-producing cells and virions released were analyzed using Western blotting (WB) with the antibodies indicated at the left of the panel. Proteins detected are indicated with arrowheads at the right of the panel. The results of a representative experiment of four independent experiments are shown.

FIG. 2C is a picture of a Western blot, wherein both virions released and lysates of virus-producing cells were analyzed for the 55-kDa Gag precursor ($Pr55^{gag}$) and products of its processing using WB with the antibodies indicated. The results of a representative experiment of three independent experiments are shown.

FIG. 2D is a bar graph demonstrating virus production based a p24 antigen capture assay. Virus production was measured in supernatants of virus-producing cells using a p24 antigen capture assay (Zeptometrix Corp, Buffalo, N.Y.) according to the manufacturer's recommendations, in duplicates. The results of a representative experiment of three independent experiments are shown.

FIG. 3A is a picture of a Western blot (WB). Virus-producing cells were transfected with control or TULA-2. siRNA as indicated and lysed, and the lysates were analyzed using WB. Proteins detected using WB are indicated with arrowheads at the right of the panel.

FIG. 3B is a bar graph demonstrating the level of infectivity. Cell supernatants were harvested, filtered and used at a dose of 10 μl to transduce $2 \times 10^5$ Jurkat cells in a total volume of 500 μl. Measurements were carried out in triplicates; mean+/−SD is shown. Infectivity of control supernatant=100%. The results of a representative experiment of two independent experiments are shown.

FIG. 4 is a picture of a Western blot demonstrating the effect of TULA on Gag expression and processing. 293T cells were transfected to express Gag, TULA and HP68/RLI in various combinations. The accessory plasmid of the lentivirus-producing system was used to express Gag. TULA and HP68/RLI were expressed using respective expression plasmids. Whole cell lysates of these cells were analyzed using WB. The antibodies used for WB and the proteins detected are indicated at the left and at the right of the figure, respectively. TULA and HP68/RLI were wild-type proteins tagged with FLAG and Myc, respectively. The results of a representative experiment of four independent experiments are shown in FIG. 4.

FIGS. 5A and 5B demonstrate the effect of TULA on the interaction of HP68/RLI and HIV-1 Gag.

FIG. 5A is a picture of a Western blot; 293T cells were transfected to express TULA, HIV-1 Gag and HP68/RLI as indicated at the top. Whole cell lysates and anti-p24 immunoprecipitates (IP) were analyzed using WB. The antibodies used for WB and the proteins detected are indicated at the left and at the right of the corresponding panels, respectively. TULA and HP68/RLI were tagged with FLAG and Myc, respectively. The amount of HP68/RLI co-immunoprecipitated with HIV-1 Gag adjusted for the amount of $Pr55^{Gag}$ in anti-p24 immunoprecipitates is shown under the corresponding panel.

FIG. 5B is a picture of a Western blot wherein the effects of wild-type TULA and [ΔUBA]TULA on co-IP of HIV-1 Gag and HP68/RLI were compared. The experiment was carried out as described in (A) with the exception that Gag-GFP was used. Gag-GFP was immunoprecipitated and immunoblotted using anti-GFP. The results of a representative experiment of three independent experiments are shown for FIGS. 5A and 5B.

FIG. 6 is a fluorescence microscopy image demonstrating the effect of TULA on the intracellular localization of HIV-1 Gag-GFP. 293T cells were grown on a glass cover slip coated with fibronectin to ~50% confluency and transfected to express HIV-1 Gag-GFP and either wild-type TULA or [ΔUBA]TULA as indicated at the top of the figure. In Gag-only cells, an empty plasmid was transfected instead of a TULA-expression plasmid. Then cells were fixed and analyzed using a fluorescent microscope. Two representative fields are shown for each transfection. The scale bar equals 10 μm.

FIGS. 7A and 7B demonstrate homology between TULA and TULA-2. FIG. 7A demonstrates homology between the amino acid sequences of TULA (SEQ ID NO: 2) and TULA2 (SEQ ID NO: 6), wherein identical amino acids are denoted by asterisks (*), dots indicate similar amino acids, a dotted line ( . . . . . . ) indicates UBA domain, a dashed line (_ _ _ _) indicates SH3 domain, and a solid line (_____) indicates HCD domain and homologues thereof. FIG. 7B demonstrates homology between the encoding polynucleotide sequences of TULA (SEQ ID NO: 1) and TULA2 (SEQ ID NO: 5), wherein a dotted line ( . . . . . . ) indicates UBA domain, a dashed line (_ _ _ _) indicates SH3 domain, and a solid line (_____) indicates HCD domain and homologues thereof.

Figure 1:
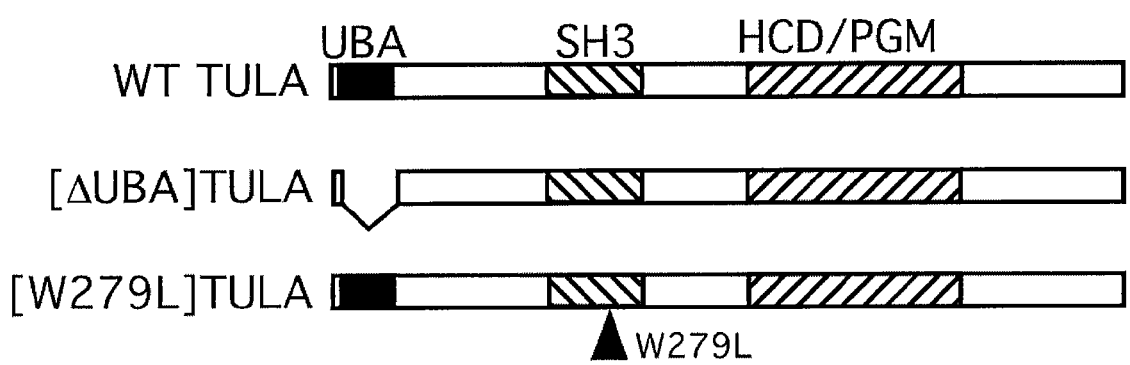
FIG. 1. is a schematic representation of TULA. UBA is a ubiquitin-associated domain. SH3 domain binds to proline-rich motifs. HCD/PGM is a region homologous to phosphoglyceromutases. [ΔUBA]TULA lacks UBA as a result of a deletion. The W279L mutation inactivates TULA's SH3 domain.

It has been observed that Gag-GFP shows punctate localization, primarily to the plasma membrane-proximal area, in the absence of TULA co-expression. Co-expression of wild-type TULA with Gag-GFP profoundly modified Gag-GFP localization; Gag-GFP accumulates in large membrane compartments, which are likely to be related to multi-vesicular bodies. In contrast, [ΔUBA]TULA does not affect Gag-GFP localization. These effects of TULA are consistent with the notion that TULA blocks the intracellular trafficking of Gag in a UBA-dependent fashion.

DETAILED DESCRIPTION OF PREFERRED EMBODIMENTS OF THE INVENTION

The present invention provides novel methods for treating retroviral infections of mammalian cells, particularly, treating infections with human immunodeficiency virus (HIV) and associated diseases, including acquired immune deficiency syndrome (AIDS).

In one aspect, the invention is a method of inhibiting a retrovirus production, the method comprising administering a retrovirus inhibitor selected from the group consisting of at least one of a TULA protein, a fragment of a TULA protein containing a UBA domain, a UBA domain of a TULA protein, a peptide mimicking a TULA protein, a peptide mimicking a fragment of a TULA protein containing a UBA domain, a peptide mimicking a UBA domain of a TULA protein, a polynucleotide encoding a TULA protein, a polynucleotide encoding a fragment of a TULA protein containing a UBA domain, a polynucleotide encoding a UBA domain of a TULA protein, a polynucleotide encoding a peptide mimicking a TULA protein, a polynucleotide encoding a peptide mimicking a fragment of a TULA protein containing a UBA domain, a polynucleotide encoding a peptide mimicking the UBA domain of TULA protein, fragments thereof, muteins thereof, variants and splice variants thereof, and combinations thereof to a cell or a tissue infected by a retrovirus.

This invention has major advantage over the strategies focused on the viral proteins, because it eliminates the problem of the high mutation rate of a retrovirus such as, for example, HIV-1, that allows it to escape recognition either by host antibodies or by drugs inhibiting viral reverse transcriptase or protease. Inventors discovered that at least the UBA domain of TULA or a fragment thereof, muteins thereof, variants and splice variants thereof are necessary for the inhibition of virus production.

Without being bound by a specific theory, inventors believe that TULA inhibits HIV-1 biogenesis by specifically interfering with the intracellular trafficking of HIV-1 Gag, a process mediated by host proteins and essential for HIV-1 production. Therefore, TULA proteins work as natural barriers to HIV-1 infection.

Knowledge that TULA proteins exert negative effect on HIV-1 infection allows for creating a new anti-HIV-1 treatment based on the anti-HIV effect of TULA. This can be done by either using the peptides that mimic the action of TULA or the expression of TULA or its fragments and muteins utilizing gene therapy methods.

This invention can be used for generating a new type of a drug for diseases caused by a retrovirus, preferably, an anti-HIV drug, based on TULA proteins or mimicking the action of TULA proteins.

TULA proteins interfere with HIV-1 production at a step common for the entire family of retroviruses. Therefore, it is believed that the negative effect of TULA is not restricted to HIV-1, HIV-2 but spans over the whole retroviral family. Thus, TULA can also be used for the treatment of retrovirus-induced cancer, for example.

The invention can be used to suppress HIV-1 production using two approaches. First, TULA or TULA fragments mediating its biological activity can be expressed in the cells infected with HIV-1 using standard techniques of gene therapy. Second, small peptides that are derived from the TULA sequence and are capable of inhibiting HIV-1 biogenesis or synthetic non-peptide molecules mimicking the effect of these peptides can be used as pharmaceuticals.

Inventors have discovered a negative effect of TULA proteins on HIV-1 biogenesis, which indicates the role of TULA in cellular defense against HIV-1 infection. Using this invention in the anti-HIV therapy may solve two problems. First, using a human protein as a drug eliminates toxic side effects and allergic reactions typically associated with using synthetic compounds. Second, targeting the invariant host proteins essential for HIV-1 biogenesis eliminates the problem linked to the high mutation rate of HIV-1 proteins.

The current drugs used for the therapy of HIV-1 infection are the chemical compounds belonging to the three major classes: (i) nucleoside/nucleotide reverse transcriptase inhibitors (NRTIs); (ii) non-nucleoside reverse transcriptase inhibitors (NNRTIs); and (iii) protease inhibitors (PIs). The novel targets for chemotherapeutic intervention are other events in viral cycle, e.g. viral adsorption, viral entry, virus-cell fusion, viral assembly and disassembly, proviral DNA integration and viral mRNA transcription.

The disadvantage of all these methods is that they are directed against viral proteins. Since all sequences encoding for HIV-1 protein are reverse-transcribed by HIV-1 Pol, all HIV-1 proteins are mutated at a rate higher than that of cellular proteins, thus being capable to eventually become insensitive to drug treatment.

Inventors have discovered a novel approach in anti-HIV therapy. The novel approach is based on the proposition not to interfere with the functions of viral proteins, but to harness the anti-viral potential of TULA, an invariant cellular protein. The advantages of this approach are that since TULA interferes not with HIV-1 proteins, but with the cellular proteins essential for HIV-1 biogenesis such as, for example, HP68/RLI, HIV-1 is unlikely to become resistant to the treatment with TULA-based drugs. Furthermore, these drugs will not likely to cause toxic or allergic reactions in treated individuals.

The invention is based on an experimental fact of TULA being a negative regulator of HIV-1 biogenesis. Based on the previous knowledge in the art, it could not be predicted that TULA is a negative regulator of HIV-1, since TULA is dissimilar to all proteins known to negatively affect HIV-1 production or infectivity.

TULA proteins inhibit maturation of HIV-1 particles. This effect can be achieved by expressing TULA in the infected cells. It is believed that the same effect will be caused by the expression of TULA fragments or treatment of the infected cells with small peptides or non-peptide compounds mimicking the effect of TULA.

Definitions

As used in this disclosure, the term "TULA proteins" includes TULA (another term is STS-2) (SEQ. ID. NO: 2) and TULA-2 (another term is STS-1) (SEQ. ID. NO: 6 and SEQ. ID. NO:19, a longer version of TULA-2), fragments thereof, muteins thereof, variants and splice variants thereof, and combinations thereof. FIGS. 7A and 7B demonstrate homology between TULA and TULA-2, wherein identical amino acids are denoted by asterisks (*), dots indicate similar amino acids, a dotted line ( . . . . . . ) indicates UBA domain, a dashed line (_ _ _ _) indicates SH3 domain, and a solid line (_____) indicates HCD domain and homologues thereof.

Nucleic Acids

One aspect of the present invention is the antiretroviral use of the polynucleotide sequences of TULA proteins and/or UBA domain of TULA proteins essentially as set forth in SEQ ID NOs: 1, 3, 5, 7, the complement of these sequences, the RNA versions of both DNA strands and the information otherwise contained within the linear sequence of these polynucleotide sequences, fragments thereof, muteins thereof, variants and splice variants thereof. The polynucleotide encoding TULA is exemplified by SEQ ID NO: 1 and the polynucleotide encoding TULA-2 is exemplified by SEQ ID NO: 5. The polynucleotide encoding UBA domain of TULA is exemplified by SEQ. ID NO: 3 and the polynucleotide encoding UBA domain of TULA-2 is exemplified by SEQ. ID NO: 7.

In the case of nucleic acid fragments, sequences for use with the present invention are those that have greater than about 50 to 60% homology with any portion of the polynucleotide sequences described herein, sequences that have between about 61% and about 70%; sequences that have between about 71 and about 80%; or between about 81% and about 90%; or between 91% and about 99%; or which contain nucleotides that are identical, functionality equivalent, or functionally irrelevant, with respect to the nucleotides present in SEQ ID NOs: 1, 3, 5, 7, are considered to be essentially similar. Also encompassed within the present invention are nucleic acids that encode polypeptides that are at least 40% identical or similar to the amino acid sequences shown in SEQ ID NOs: 1, 3, 5, and 7.

As used herein, the term "a splice variant" refers to variant TULA proteins and/or UBA domain of TULA proteins-encoding nucleic acid(s) produced by differential processing of primary transcript(s) of genomic DNA, resulting in the production of more than one type of mRNA. cDNA derived from differentially processed primary transcript will encode TULA proteins and/or UBA domain of TULA proteins subtypes that have regions of complete amino acid identity and regions having different amino acid sequences. Thus, the same genomic sequence can lead to the production of multiple, related mRNAs and proteins. Both the resulting mRNAs and proteins are referred to herein as "splice variants." For example, TULA has two different alternative splice isoforms which differ by 38 amino acids in the region between UBA and SH3 (Accession Number for the long form sequence is NP_061834, and Accession Number for the short form is NP_001001895) (see also Wattenhofer et al. (2001) and Feshchenko et al. (2004)). In the present application, the experiments were carried out with the short isoform of TULA, because this form is prevalent in T cells (Feshchenko et al., 2004).

Muteins of TULA proteins and/or UBA domain of TULA proteins which do not destroy the activity of the protein may be used as the active treating substance of the instant invention. Muteins are prepared by modification of the primary structure of the protein itself, by deletion, addition, or alteration of the amino acids incorporated into the sequence during translation. For example, at least one cysteine residue of TULA proteins and/or UBA domain of TULA proteins may be replaced with a conservative amino acid, in order to eliminate sites of undesirable intramolecular disulfide bond formation. Crosslinking is undesirable if it changes the conformation of TULA proteins and/or UBA domain of TULA proteins so as to render the protein essentially inactive for purposes of treating an immune system disorder. Also, it may be desirable to replace a methionine which is not essential to bioactivity with a conservative amino acid. As referred to herein, a conservative amino acid alteration is defined as one which does not significantly adversely affect biological activity and involves substitutions of the amino acid. The conservative amino acid that may be substituted for cysteine and methionine include at least: serine, alanine, glycine, valine, threonine, leucine, isoleucine, and tyrosine. More preferably they include serine and alanine. Most preferably, cysteine may be replaced with serine or alanine and methionine replaced with alanine.

The invention also encompasses other nucleic acids or nucleic acid like molecules that are sufficient in any regard to mimic, substitute for, or interfere with the TULA proteins polynucleotide sequences, as exemplified by SEQ ID NOs: 1, 3, 5, and 7 or fragments thereof. It will also be understood that the nucleic acid and amino acid sequences may include additional residues, such as additional 5'- or 3'-sequences, and yet still be essentially as set forth in one of the sequences disclosed herein, so long as the sequence meets the criteria set forth, including the maintenance of functionality, or for the purpose of engineering altered functionality with respect to TULA proteins and/or UBA domain of TULA proteins.

Included within the invention are DNA or RNA segments including oligonucleotides, polynucleotides and fragments thereof, including DNA or RNA or nucleic acid-like sequences of genomic or synthetic origin, single or double stranded. The invention includes nucleic acid molecules, or nucleic acid-like molecules that are able to hybridize to the sequences in SEQ ID NOs: 1, 3, 5, and 7 under stringent or under permissive hybridization conditions, or to the complement of said sequences.

The invention also includes oligonucleotide, or oligonucleotide-like sequences such as phosphorthioate, or peptide nucleic acid sequences, which possess sufficient similarity with the sequences disclosed herein such that they are able to stably hybridize to the disclosed sequences, or their complements. Such sequences may be intended as antisense regulators of gene expression, or for the selective amplification or extension of adjoining sequences, for instance by PCR using a given annealing temperature, as would be determined by someone skilled in the art. In addition to the sequences disclosed here, related sequences in other organisms, or homologs, will be readily identified by hybridization using the present sequences. Similar techniques will also apply to the identification of mutant alleles, polymorphisms, deletions, insertions, and so forth, in genomic and cDNA sequences. Whole or partial sequences referred to above may also be identified and isolated using techniques that involve annealing of short oligonucleotides to complementary sequences, such as those as might be present in the genomic DNA of a particular organism, or in genomic or cDNA, including expression cDNA, libraries. Thus, PCR is used to obtain DNA sequences homologous to, and which lie between, two primers, usually between 15 to 30 nucleotides which have annealing temperatures typically between 60-80 degrees Celsius may be substantially purified.

It will be understood that this invention is not limited to the particular nucleic acid sequences presented herein. Recombinant vectors, including for example plasmids, phage, viruses, and other sequences, and isolated DNA or RNA segments may therefore variously include the TULA proteins gene sequences or their complements, and coding regions, as well as those that may bear selected alterations or modifications that nevertheless include TULA proteins segments or may encode biologically or experimentally relevant amino acid sequences. Such sequences may be created by the application of recombinant DNA technology, where changes are engineered based on the consideration of the nucleotides or amino acids being exchanged, deleted, inserted, fused, or otherwise modified.

In yet another aspect, the invention is an antigenic fragment of an isolated peptide sequence encoded by a polynucleotide selected from the group consisting of SEQ ID NO: 1, SEQ ID NO:3, SEQ ID NO:5, SEQ ID NO:7, fragments thereof, muteins thereof, variants and splice variants thereof, and combinations thereof. In certain embodiments, the antigenic fragment inhibits maturation of HIV-1.

Proteins and Polypeptides

One aspect of the invention is the protein, polypeptide, oligopeptide, or amino acid sequences or fragments thereof, of TULA proteins and/or UBA domain of TULA proteins, essentially as set forth in SEQ ID NOs: 2, 4, 6, 8, and 19. The TULA polypeptide is exemplified by SEQ ID NO: 2, the TULA-2 polypeptide is exemplified by SEQ ID NOs: 6 and 19, the UBA domain of TULA polypeptide is exemplified by SEQ ID NO: 4, and the UBA domain of TULA-2 polypeptide is exemplified by SEQ ID NO: 8. Sequences that have greater than about 40-50% homology with any portion of the amino acid sequences described herein, sequences that have between about 51% and about 60%; sequences that have between about 61% and about 70% sequences that have between about 70 and about 80%; or between about 81% and about 90%; or between 91% and about 99%; or those that contain amino acids that are identical, functionally equivalent, or functionally irrelevant, for instance those specified by conservative, evolutionarily conserved, and degenerate substitutions, with respect to the amino acid sequences presented in SEQ ID NOs: 2, 4, 6, 8 and 19 are included. The invention thus applies to TULA and/or UBA polypeptide sequences, fragments thereof, muteins thereof, and nucleic acids which encode such polypeptides, such as those of other species. Reference is particularly, but not exclusively, made to the conserved regions of TULA and/or UBA, in contrast to similarity throughout the entire length. The invention thus encompasses amino acid sequences, or amino acid-like molecules, that are sufficient in any regard to mimic, substitute for, or interfere with maturation of HIV.

The invention encompasses TULA and/or UBA amino acid sequences that have been altered in any form, either through the use of recombinant engineering, or through post-translational or chemical modifications, including those that may be produced by natural, biological, artificial, or chemical methods. Naturally, it will be understood that this invention is not limited to the particular amino acid sequences presented herein. Altered amino acid sequences include those which have been created by the application of recombinant technology such that specific residues, regions, or domains have been altered, and which may be functionally identical, or which may possess unique biological or experimental properties with regards to function or interactions with natural and artificial ligands.

For instance such modifications may confer longer or shorter half-life, reduced or increased sensitivity to ligands that modify function, ability to detect or purify polypeptides, solubility, and so forth. Alternatively, such sequences may be shorter oligopeptides that possess an antigenic determinant, or property that interferes, or competes, with the function of a larger polypeptide, and those that affect maturation of HIV. Such sequences may be created by the application of the nucleotides or amino acids being exchanged, deleted, inserted, fused, or otherwise modified. Likewise, the current invention within, the sequences that may be naturally present as extensions of, or insertions within, the sequences disclosed herein, including alternative or longer N- and C-terminal sequences, or alternatively spliced protein isoforms.

Production and purification of polypeptides may be achieved in any of a variety of expression systems known to those skilled in the art, including recombinant DNA techniques, genetic recombination, and chemical synthesis. For instance, expression in prokaryotic cells may be achieved by placing protein coding nucleic sequences downstream of a promoter, such as T7, T3, lacI, lacZ, trp, or other cellular, viral, or artificially modified promoters including those that may be inducible by IPTG, tetracycline, maltose, and so forth. Such promoters are often provided for in commercially available recombinant DNA vectors such as pRSET ABC, pBluescript, pKK223-3, and others, or are easily constructed to achieve such a purpose, and often include the presence of multiple cloning sites (MCS) to facilitate typically contain efficient ribosome binding sites, and in some cases transcription termination signals.

Peptides, oligopeptides and polypeptides may also be produced by chemical synthesis, for instance solid phase techniques, either manually or under automated control such as Applied Biosystems 431 peptide synthesizer (Perkin Elmer). After synthesis, such molecules are often further purified by preparative high performance liquid chromatography. Thus, the invention provides methods for the production of epitopes for antibody production, or the production of small molecules that enhance or interfere with a specific function or interaction of the TULA and/or UBA polypeptides.

Methods to produce and purify said polypeptides in eukaryotic systems are widely available and understood by those proficient in the art. Cells for such production are known to include yeast and other fungi, Drosophila and Sf9 cells, cells of other higher eukaryotic organisms such as HeLa, COS, CHO and others, as well as plant cells. Similarly, expression could be achieved in prokaryotic or eukaryotic extracts that are able to translate RNAs into proteins, such as rabbit reticulocyte lysates.

In yet another aspect, the invention is an antigenic fragment of an isolated peptide sequence, wherein the antigenic fragment is from a peptide selected from the group consisting of SEQ ID NO: 2, SEQ ID NO:4, SEQ ID NO:6, SEQ ID NO:8, SEQ ID NO: 19 fragments thereof, muteins thereof, variants and splice variants thereof, and combinations thereof. In certain embodiments, the antigenic fragment inhibits maturation of HIV-1.

In yet another aspect, the invention is a substantially purified polypeptide selected from the group consisting of SEQ ID NO: 2, SEQ ID NO:4, SEQ ID NO:6, SEQ ID NO:8, SEQ ID NO: 19 fragments thereof, muteins thereof, variants and splice variants thereof, and combinations thereof.

Vectors, Host Cells and Cell Lines

In another aspect, the invention is a host cell comprising a retrovirus inhibitor selected from the group consisting of at least one of a TULA protein, a fragment of a TULA protein containing a UBA domain, a UBA domain of a TULA protein, a peptide mimicking a TULA protein, a peptide mimicking a fragment of a TULA protein containing a UBA domain, a peptide mimicking a UBA domain of a TULA protein, SEQ ID NO: 2, SEQ ID NO: 4, SEQ ID NO: 6, SEQ ID NO: 8, SEQ ID NO: 19, fragments thereof, muteins thereof, variants and splice variants thereof, and combinations thereof, wherein the retrovirus inhibitor modulates retrovirus production. In certain embodiments, the host cell is a member selected from the group consisting of eukaryotic cells and prokaryotic cells.

In yet another aspect, the invention is a host cell line stably transfected with a TULA protein, a fragment of a TULA protein containing a UBA domain, a UBA domain of a TULA protein, a peptide mimicking a TULA protein, a peptide mimicking a fragment of a TULA protein containing a UBA domain, a peptide mimicking a UBA domain of a TULA protein, SEQ ID NO: 2, SEQ ID NO: 4, SEQ ID NO: 6, SEQ ID NO: 8, SEQ ID NO: 19, fragments thereof, muteins thereof, variants and splice variants thereof, and combinations thereof.

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC®. 2.0 from INVITROGEN® and BACPACK® BACULOVIRUS EXPRESSION SYSTEM FROM CLONTECH.

Vectors may be of bacterial origin, which may comprise a promoter of a bacteriophage such as phage or T7 which is capable of functioning in the bacteria. In one of the most widely used expression systems, the nucleic acid encoding the TULA proteins may be transcribed from the vector by T7 RNA polymerase (Studier et al, Methods in Enzymol. 185: 60-89, 1990). In the E. coli BL21 (DE3) host strain, used in conjunction with pET vectors, the T7 RNA polymerase is produced from the 1-lysogen DE3 in the host bacterium, and its expression is under the control of the IPTG inducible lac UV5 promoter. This system has been employed successfully for over-production of many proteins. Alternatively, the polymerase gene may be introduced on a lambda phage by infection with an int-phage such as the CE6 phage, which is commercially available (Novagen, Madison, USA). Other vectors include vectors containing the lambda PL promoter such as PLEX® (Invitrogen, NL), vectors containing the trc promoters such as pTrcH is Xpress® (Invitrogen), or pTrc99 (Pharmacia Biotech, SE), or vectors containing the tac promoter such as pKK223-3 (Pharmacia Biotech), or PMAL (New England Biolabs, MA., USA).

One of skill in the art will understand that cloning also requires the step of transforming a host cell with a recombinant nucleic acid molecule. A host cell is "transformed" by a nucleic acid when the nucleic acid is translocated into the cell from the extracellular environment. Any method of transferring a nucleic acid into the cell may be used; the term, unless otherwise indicated herein, does not imply any particular method of delivering a nucleic acid into a cell, nor that any particular cell type is the subject of transfer. For example, bacterial host cells, such as E. coli HB101, can be transformed by electroporation using any commercially-available electroporation apparatus known in the art, such as a GenePulser apparatus (Bio-Rad, Hercules, Calif.). In one embodiment, mammalian cells, such as BHK-21 cells or Vero cells (ATCC CCL-81), are transformed with a recombinant plasmid containing a cloned cDNA by the method of "transfection." The term "transfection" refers to the transfer of genetic material into a eukaryotic cell, such as a mammalian cell, from the external environment of the cell.

One of skill in the art will appreciate the variety of methods of transfection that are available in the art. Such methods include the nucleic acid/CaPO4 co-precipitation method, the diethylaminoethyl (DEAE)-dextran method, the polybrene method, the cationic liposome method ("lipofection"), the electroporation method, the microinjection method, and the microparticle bombardment method. A description of transfection methods can be found in M. A. Aitken et al., Molecular Biomethods Handbook, Chapter 20, p. 235-250.

According to another embodiment of the instant invention, in vitro transcription is carried out on a recombinant plasmid carrying a cloned cDNA of the invention, under the control of an expressible promoter (i.e., a promoter which is effectively enabled or activated in vitro in the presence of corresponding transcription factors and RNA polymerase). The transcription process generates a fully-infectious mRNA transcript that can be used to transfect (i.e., infect) a cell host, such as BHK-21 (hamster kidney cells) or Vero cells. In one embodiment, the cDNA is operably linked with the bacteriophage transcriptional promoter, T7; to enable the in vitro transcription of the cDNA using bacteriophage T7 DNA-dependent RNA polymerase. One of ordinary skill in the art will appreciate that any suitable promoter, such as, for example, SP6, T3, any bacterial, viral, phage, or eukaryotic promoter, for controlling the transcription of, for example, TULA and/or UBA gene, or fragment thereof, and for controlling the expression of a nucleotide sequence encoding a reporter is contemplated by the present invention. It will be appreciated that the promoter is typically selected from promoters which are functional in mammalian cells susceptible to infection by TULA and/or UBA gene, or fragment thereof, encoding sequences of the invention, although prokaryotic or phage promoters and promoters functional in other eukaryotic cells may be used. The promoter is typically derived from promoter sequences of viral or eukaryotic genes. For example, it may be a promoter derived from the genome of a cell in which expression or transcription of, for example, TULA and/or UBA gene, or fragment thereof, encoding sequence or construct is to occur.

With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). Tissue-specific or cell-specific promoters specific for lymphocytes, dendritic cells, skin, brain cells and epithelial cells, for example the CD2, CD11c, keratin 14, and Wnt-1, respectively. Preferably the epithelial cell promoter SPC is used. They may also be promoters that respond to specific stimuli, for example promoters that bind steroid hormone receptors. Viral promoters may also be used, for example the Moloney murine leukaemia virus long terminal repeat (MMLV LTR) promoter, the Rous sarcoma virus (RSV) LTR promoter, the human cytomegalovirus (CMV) IE promoter, or SV40 promoter.

It may also be advantageous for the promoters to be inducible so that the levels of expression of, for example, the TULA and/or UBA gene, or fragment thereof encoding sequence can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above. It will be appreciated that the sources of promoter sequences, which typically can be retrieved using recombinant techniques from different cloning vectors and plasmids, etc., can be obtained from commercial sources, such as, NEW ENGLAND BIOLABS, INC. (MA), PROMEGA CORPORATION (WI), or BD BIOSCIENCES (CA), or from the laboratories of academic research groups upon request.

The invention also relates to cells which contain such recombinant constructs, where the host cell refers to mammalian, plant, yeast, insect, or other eukaryotic cells, or to prokaryotic, or archae, and vectors that are designed for a given host. Promoter-vector combinations could be chosen by a person skilled in these arts. In some cases, the desired outcome may not be protein, but RNA, and recombinant vectors would include those with inserts present in either forward or reverse orientations.

Many of the vectors and hosts have specific features that facilitate expression or subsequent purification. For instance DNA sequences to be expressed as proteins often appear as fusion with unrelated sequences that encode polyhistidine tags, or HA, FLAG, myc and other epitope tags for immunochemical purification and detection, or phosphorylation sites, or protease recognition sites, or additional protein domains such as glutathione S-transferase (GST), maltose binding protein (MBP), and so forth which facilitate purification. Vectors may also be designed which contain elements for polyadenylation, splicing and termination, such that incorporation of naturally occurring genomic DNA sequences that contain introns and exons can be produced and processed, or such that unrelated introns and other regulatory signals require RNA processing prior to production of mature, translatable RNAs. Proteins produced in the systems described above could be subject to a variety of post-translational modifications, such as glycosylation, phosphorylation, nonspecific or specific proteolysis or processing.

Purification of TULA and/or UBA vectors, or variants produced as described above can be achieved by any of several widely available methods. Cells may be subject to freeze-thaw cycles or sonication to achieve disruption, or may be fractionated into subcellular components prior to further purification. Purification may be achieved by one or more techniques such as precipitation with salts or organic solvents, ion exchange, hydrophobic interaction, HPLC and FPLC chromatograpic techniques. Affinity chromatographic techniques could include the use of polyclonal or monoclonal antibodies raised against the expressed polypeptide, or antibodies raised against or available for an epitopic tag such as HA or FLAG. Similarly, purification can be aided by affinity chromatography using fusions to the desired proteins such as GSH-affinity resin, maltose affinity resin, carbohydrate (lectin) affinity resin or, in a one embodiment, Ni-affinity resin, and so forth. In some instances purification is achieved in the presence of denaturing agents such as urea or guanidine, and subsequent dialysis techniques may be required to restore functionality, if desired.

Any method of in vitro transcription known to one of ordinary skill in the art is contemplated by the instant invention. It will be understood that the method of in vitro transcription of a DNA sequence relies on the operable linkage to an appropriate promoter and that the cognate RNA polymerase is used to direct transcription of the DNA starting at the promoter sequence. It will be further appreciated that the RNA polymerase and promoter can be of bacterial, eukaryotic, or viral (including bacteriophage) origin. Bacteriophage-RNA polymerases are very robust, and the availability of purified recombinant proteins facilitates the generation of large quantities of RNA from cloned cDNA sequences. In contrast, eukaryotic in vitro transcription systems yield relatively small quantities of RNA. Bacteriophage-RNA polymerases, such as from bacteriophages SP6, T7, and T3, are especially suitable for the generation of RNA from DNA sequences cloned downstream of their specific promoters because, first, their promoters are small and easily incorporated into plasmid vectors and second, the polymerases are quite specific for their cognate promoters, which results in very little incorrect transcriptional initiation from DNA templates. Any suitable promoter, however, is contemplated by the instant invention, including, for example, bacterial, phage, viral, and eukaryotic promoters. Strong termination sequences are not available for these polymerases so that DNA templates can be linearized with a restriction enzyme 3' to the desired end of the RNA transcript and the polymerase is forced to stop at this point-a process referred to as "run-off" transcription. A full description of in vitro transcription can be found in M. A. Aitken et al., Molecular Biomethods Handbook, Chapter 26, p. 327-334 and Sambrook, J. and D. W. Russell, Molecular Cloning: A Laboratory Manual, Third Edition (2001).

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5 alpha, JM 109, and KC8, as well as a number of commercially available bacterial hosts such as SURE®. Competent Cells and SOLOPACK® Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12, etc. Many host cells from various cell types and organisms are available and would be known to one of skill in the art. Similarly, a viral vector may be used in conjunction with either a eukaryotic or prokaryotic host cell, particularly one that is permissive for replication or expression of the vector.

In certain cases, alteration of a genomic sequence in a pluripotent cell (e.g., a hematopoietic stem cell) is desired. Methods for mobilization, enrichment and culture of hematopoietic stem cells are known in the art. See for example, U.S. Pat. Nos. 5,061,620; 5,681,559; 6,335,195; 6,645,489 and 6,667,064.

Diagnostic and Treatment Kits

A diagnostic or a treatment system in a form of a kit is also contemplated in this invention. Thus, in another aspect, the invention is a kit for inhibiting production of a retrovirus in a cell or a tissue infected by a retrovirus, the kit comprising a retrovirus inhibitor selected from the group consisting of at least one of a TULA protein, a fragment of a TULA protein containing a UBA domain, a UBA domain of a TULA protein, a peptide mimicking a TULA protein, a peptide mimicking a fragment of a TULA protein containing a UBA domain, a peptide mimicking a UBA domain of a TULA protein, a polynucleotide encoding a TULA protein, a polynucleotide encoding a fragment of a TULA protein containing a UBA domain, a polynucleotide encoding a UBA domain of a TULA protein, a polynucleotide encoding a peptide mimicking a TULA protein, a polynucleotide encoding a peptide mimicking a fragment of a TULA protein containing a UBA domain, a polynucleotide encoding a peptide mimicking the UBA domain of TULA protein, fragments thereof, muteins thereof, variants and splice variants thereof, and combinations thereof; and instructions for administering the retrovirus inhibitor.

In certain embodiments of the kit, the retrovirus inhibitor is encoded by at least one of SEQ ID NO: 1, SEQ ID NO: 3, SEQ ID NO: 5, SEQ ID NO: 7, fragments thereof, muteins thereof, variants and splice variants thereof, and combinations thereof.

In certain embodiments of the kit, the retrovirus inhibitor is at least one of SEQ ID NO: 2, SEQ ID NO: 4, SEQ ID NO: 6, SEQ ID NO: 8, SEQ ID NO: 19 fragments thereof, muteins thereof, variants and splice variants thereof, and combinations thereof.

In certain embodiments, the kit further comprises the cell or the tissue infected by a retrovirus. In certain embodiments, the retrovirus is HIV-1.

A diagnostic or a treatment system in kit form of the present invention includes, in an amount sufficient for at least one assay, a polypeptide, antibody composition or monoclonal antibody composition of the present invention, as a packaged reagent. Instructions for use of the packaged reagent are also typically included.

As used herein, the term "package" refers to a solid matrix or material such as glass, plastic, paper, foil and the like capable of holding within fixed limits a polypeptide, antibody composition or monoclonal antibody composition of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody. "Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic or a treatment system of the present invention further includes a label or indicating means capable of signaling the formation of a complex containing a polypeptide or antibody molecule of the present invention. The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel proteins methods and/or systems. The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{111}$indium or $^{3}H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas, et al., Scand. J. Immunol., Vol. 8 Suppl. 7:7-23 (1978), Rodwell et al., Biotech., 3:889-894 (1984), and U.S. Pat. No. 4,493,795, which are all incorporated herein by reference.

The diagnostic or a treatment kits of the present invention can be used in an "ELISA" format to detect, for example, the presence or quantity of TULA and/or UBA in a body fluid sample such as serum, plasma, or urine, etc. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of Basic and Clinical Immunology by D. P. Sites et al., published by Lange Medical Publications of Los Altos, Calif. in 1982 and in U.S. Pat. Nos. 3,654,090; 3,850,752; and 4,016,043, which are all incorporated herein by reference.

Thus, in preferred embodiments, a polypeptide, antibody molecule composition or monoclonal antibody molecule composition of the present invention can be affixed to a solid matrix to form a solid support that comprises a package in the subject diagnostic systems.

The reagent is typically affixed to the solid matrix by adsorption from an aqueous medium although other modes of affixation, well known to those skilled in the art, can be used. Useful solid matrices are also well known in the art. Such materials are water insoluble and include cross-linked dextran; agarose; beads of polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The packaging materials discussed herein in relation to diagnostic or a treatment systems are those customarily utilized. Such materials include glass and plastic (e.g., polyethylene, polypropylene and polycarbonate) bottles, vials, plastic and plastic-foil laminated envelopes and the like. In one embodiment a diagnostic or a treatment system of the present invention is useful for assaying for the presence of TULA and/or UBA. Such a system comprises, in kit form, a package containing an antibody to TULA and/or UBA.

Target Antigens

An embodiment of the present invention relates to an antibody that binds to a TULA and/or UBA protein. A typical amino acid sequence of TULA and/or UBA protein is shown in SEQ ID NOs: 2, 4, 6, 8. That is, an antibody according to the first embodiment of the present invention is preferably an antibody that specifically binds to, for example, the TULA and/or UBA polypeptide. Full length TULA protein is exemplified in SEQ ID NO: 2 and SEQ ID NO: 6, and variants, fragments, muteins, etc., and those proteins derived from this protein. It is known that humans have a diversity of allele mutations and those proteins with one or more amino acids substituted, deleted, inserted, or added are also included in the TULA and/or UBA protein. However, it is not limited to these.

Fragments of the TULA and/or UBA protein may serve as the target antigen for the antibody binding. These antigen fragments may be about 6, 7, 8, 9, 10, 11, 12, 13, 14, 15, 16, 17, 18, 19, or 20 amino acids in length. The antigen fragments may by about 10, 20, 30, 40, 50, or 100 amino acids in length. The antibody of the present invention may be either a polyclonal antibody or a monoclonal antibody. Molecule species are not particularly limited. Immunoglobulins of any class, subclass or isotype may be used.

Antibodies and Antibody Compositions

Additionally, the present invention includes a purified antibody produced in response to immunization with TULA and/or UBA, as well as compositions comprising this purified antibody.

Antibodies refer to single chain, two-chain, and multi-chain proteins and glycoproteins belonging to the classes of polyclonal, monoclonal, chimeric, and hetero immunoglobulins; it also includes synthetic and genetically engineered variants of these immunoglobulins. "Antibody fragment" includes Fab, Fab', F(ab')2, and Fv fragments, as well as any portion of an antibody having specificity toward a desired target epitope or epitopes. A humanized antibody is an antibody derived from a non-human antibody, typically murine, that retains or substantially retains the antigen-binding properties of the parent antibody but which is less immunogenic in humans, U.S. Pat. No. 5,530,101, incorporated herein by reference in its entirety.

An antibody composition of the present invention is typically produced by immunizing a laboratory mammal with an inoculum of the present invention and to thereby induce in the mammal antibody molecules having the appropriate polypeptide immunospecificity. The polyclonal antibody molecules are then collected from the mammal and isolated to the extent desired by well known techniques such as, for example, by immunoaffinity chromatography. The antibody composition so produced can be used in, inter alia, the diagnostic methods and systems of the present invention to detect TULA and/or UBA in a body sample.

Monoclonal antibody compositions are also contemplated by the present invention. A monoclonal antibody composition contains, within detectable limits, only one species of antibody combining site capable of effectively binding TULA and/or UBA. Thus, a monoclonal antibody composition of the present invention typically displays a single binding affinity for TULA and/or UBA even though it may contain antibodies capable of binding proteins other than TULA and/or UBA. Suitable antibodies in monoclonal form, typically whole antibodies, can also be prepared using hybridoma technology described by Niman et al., Proc. Natl. Sci., U.S.A., 80:4949-4953 (1983), which description is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a polypeptide of this invention.

The antibody compositions produced by the above method can be used, for example, in diagnostic and therapeutic modalities wherein formation of TULA and/or UBA containing immunoreaction product is desired.

Diagnostic Use

In another embodiment of the present invention, measurement of TULA and/or UBA, or proteins which are immunologically related to TULA and/or UBA, can be used to detect and/or stage a disease or disorder in a subject. The measured amount of the soluble molecule or of the total marker is compared to a baseline level. This baseline level can be the amount which is established to be normally present in the body fluid of subjects with various degrees of the disease or disorder. An amount present in the body fluid of the subject which is similar to a standard amount, established to be normally present in the body fluid of the subject during a specific stage of the disease or disorder, is indicative of the stage of the disease in the subject. The baseline level could also be the level present in the subject prior to the onset of disease or the amount present during remission of disease, or from individuals not afflicted with the disease or condition.

The present invention also provides for the detection or diagnosis of disease or the monitoring of treatment by measuring the amounts of TULA and/or UBA transcript or peptide in a sample before and after treatment, and comparing the two measurements. The change in the levels of the markers relative to one another can be an improved prognostic indicator. A comparison of the amounts of a total marker with the amount of intra-cytoplasmic marker or membrane-bound marker is also envisioned.

The present invention provides a method for monitoring the effect of a therapeutic treatment on a subject who has undergone the therapeutic treatment. This method comprises measuring at suitable time intervals the amount of a soluble molecule or soluble fragment thereof, or the amount of TULA and/or UBA or fragment thereof. Any change or absence of change in the amount of the soluble molecule or in the amount of the TULA and/or UBA can be identified and correlated with the effect of the treatment on the subject. In a specific embodiment of the invention, soluble molecules immunologically related to TULA and/or UBA can be measured in the serum of patients by a sandwich enzyme immunoassay (for an example) in order to predict disease prognosis, for example, in viral infections, inflammation, autoimmune diseases, and tumors, or to monitor the effectiveness of treatments such as anti-viral administration.

Pharmaceutical Compositions, Kits and Administration Thereof

In yet another aspect, the invention is a method of treating a disorder selected from the group consisting of viral infections, HIV infection, AIDS, autoimmune disease, and cancer comprising administering to said subject a therapeutically effective amount of composition comprising: (i) a first retrovirus inhibitor selected from the group consisting of at least one of a TULA protein, a fragment of a TULA protein containing a UBA domain, a UBA domain of a TULA protein, a peptide mimicking a TULA protein, a peptide mimicking a fragment of a TULA protein containing a UBA domain, a peptide mimicking a UBA domain of a TULA protein, a polynucleotide encoding a TULA protein, a polynucleotide encoding a fragment of a TULA protein containing a UBA domain, a polynucleotide encoding a UBA domain of a TULA protein, a polynucleotide encoding a peptide mimicking a TULA protein, a polynucleotide encoding a peptide mimicking a fragment of a TULA protein containing a UBA domain, a polynucleotide encoding a peptide mimicking the UBA domain of TULA protein, fragments thereof, muteins thereof, variants and splice variants thereof, and combinations thereof; and (ii) a pharmaceutically acceptable carrier.

In certain embodiments, the composition further comprises a second retrovirus inhibitor selected from those commonly used. A variety of anti-retroviral agents are known in the art. Most of these inhibit the activity of retroviral reverse transcriptase and include zidovudine (AZT), an analogue of thymidine, dideoxyinosine (ddI), and dideoxycytosine (ddC). Zidovudine is the primary anti-viral drug used in the treatment of HIV infection. Anti-retroviral agents are generally efficacious in a dose ranging from about 50 mg/day to about 1000 mg/day, more particularly from about 100 mg/day to about 500 mg/day, and in the case of zidovudine, specifically about 300 mg/day to about 500 mg/day. These agents are generally administered in oral formulations.

Administration of therapeutically effective amounts is by any of the routes normally used for introducing protein or encoding nucleic acids into ultimate contact with the tissue and/or cells to be treated. The protein or encoding nucleic acids are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., Remington's Pharmaceutical Sciences, 17th ed. 1985)).

The protein or encoding nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The pharmaceutical compositions can be prepared by methods known in the art, including, by way of an example, the simple mixing of reagents. Those skilled in the art will know that the choice of the pharmaceutical carrier and the appropriate preparation of the composition depend on the intended use and mode of administration.

In one embodiment, it is envisioned that the compound and pharmaceutically acceptable carrier constitute a physiologically-compatible, slow-release formulation. The primary solvent in such a carrier can be either aqueous or non-aqueous in nature. In addition, the carrier can contain other pharmacologically-acceptable excipients for modifying or maintaining the pH, osmolarity, viscosity, clarity, color, sterility, stability, rate of dissolution, or odor of the formulation. Similarly, the carrier can contain still other pharmacologically-acceptable excipients for modifying or maintaining the stability, rate of dissolution, release, or absorption of the compound. Such excipients are those substances usually and customarily employed to formulate dosages for oral, parenteral or local administration in either unit dose or multi-dose form.

Once the pharmaceutical composition has been formulated, it can be stored in sterile vials as a solution, suspension, gel, emulsion, solid, or dehydrated or lyophilized powder. Such formulations can be stored either in a ready to use form or requiring reconstitution immediately prior to administration.

In this invention, effect of TULA on production of retroviruses was studied based on production of pseudotyped HIV-1 based lentiviruses. It was found that overexpression of TULA decreases virus production.

To assess the effect of TULA on HIV-1 biogenesis, HIV-1 was produced in 293T cells in the presence of overexpressed TULA or its mutants (FIG. 1). 293T cells were transfected with the expression plasmid encoding for wild-type or mutant TULA along with the plasmids required to produce recombinant HIV-1 virus: HIV-1 based gene transfer plasmid, plasmid encoding for GAG-Pol and viral accessory genes and a VSVG-envelope encoding plasmid. It was observed that VSVG-pseudotyped HIV-1 virus produced in this system was capable of infecting a wide variety of cell types.

For quantification of virus production, several complimentary approaches were employed. First, inventors used the single-round infectivity assay. For this assay, supernatants of transfected cells were harvested and used to infect Jurkat cells in a wide range of doses (multiplicity of infection from ~0.01 to ~1). Because the infection cannot spread beyond one cycle in this system, the number of infected cells is proportional to the viral titer within its linear range. This single-round infectivity assay has been used in many HIV-1-related studies; for example, it was used to show the effect of POSH ubiquitin-protein ligase on the production of pseudotyped HIV-1 viral particles [12]. (See [13, 14] for the detailed description of this approach.) The percentage of infected Jurkat cells determined by flow cytometry as GFP-positive was used to compare titers of the virus produced by 293T cells transfected to express various forms of TULA (FIG. 2A).

Figure 2A:
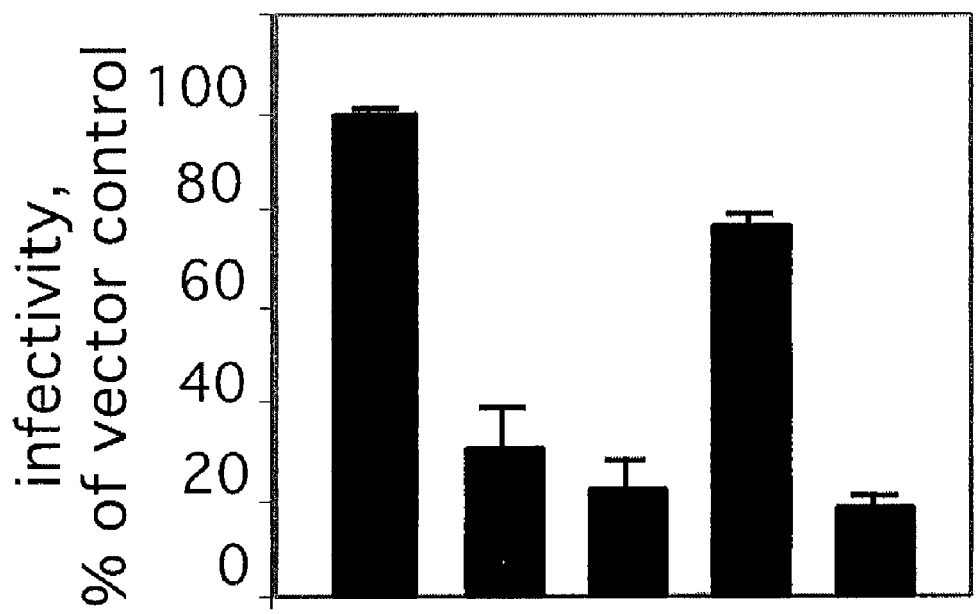
FIGS. 2A-2D demonstrate effect of TULA proteins on the production of HIV-1 based lentivirus. 293T cells were co-transfected with the three plasmids required for the production of HIV-1-based VSVG-pseudotyped lentivirus plus an expression plasmid for one of the examined proteins as indicated in all panels.

In the experiment shown in FIG. 2A, overexpression of wild-type TULA reduced the viral titer in supernatants by 3-fold as compared to that in the supernatants of vector control cells. [ΔUBA]TULA, lacking the UBA domain, did not significantly affect virus production. In contrast [W279L] TULA, lacking functional SH3 as a result of a point mutation, reduced HIV-1 titers to the same degree as wild-type TULA did. This allowed inventors to conclude that the UBA domain is necessary for the antiviral effect of TULA, whereas the SH3 domain is dispensable for this function. TULA-2 reduced viral titer to a higher extent than in case of TULA; this result indicates that the inhibitory effect on HIV-1 biogenesis is not restricted to a particular TULA family member.

To assure that TULA proteins were expressed in virus-producing 293T cells, lysates of these cells were analyzed using Western blotting (FIG. 2B); all forms of TULA were expressed at a high level. The level of GFP was constant throughout the experiment, indicating equal transfection efficiency of samples.

Figure 2B:
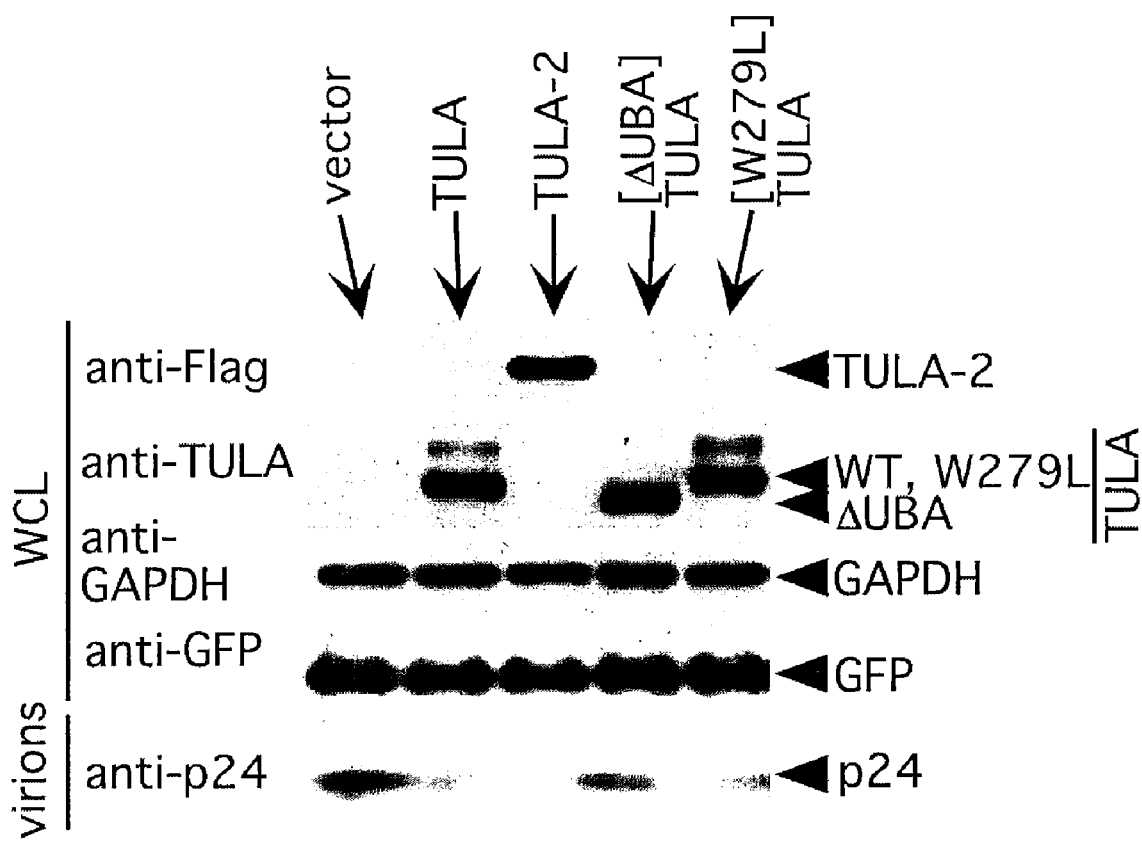

To determine whether the effect of TULA proteins on virus production was related to decrease in the infectivity or production of HIV-1 like virus in the cells, an approach allowing quantifying the amount of produced virus was utilized. Viral particles were isolated from supernatants of virus-producing cells using ultracentrifugation through a 20% sucrose cushion. The amount of virus was determined using anti-p24 Western blotting; the level of p24 in the viral particles produced by cells overexpressing TULA or TULA-2 was reduced significantly as compared to that produced by vector control cells (FIG. 2B, the lower panel).

To determine whether the observed effect of TULA was caused by a change in the total expression of Gag, Gag was analyzed in viral particles and cell lysates. The experiment shown in FIG. 2C indicates a modest effect of TULA expression on cellular Gag (both $Pr55^{Gag}$ and total Gag). In contrast, the effect of TULA on the amount of P24 and p17 in viral particles was profound even after these amounts were normalized for the amount of $Pr55^{Gag}$ or total Gag in cell lysates. Therefore, it is clear that the effect of TULA on virus production is not mediated by an overall decrease in Gag expression.

To corroborate the results obtained using Western blotting, similar experiments were carried out using a p24 antigen capture assay to measure the amount of produced virus. These experiments showed a significant decrease in the level of p24 in supernatant of virus-producing cells (FIG. 2D), thus confirming the results of single-round infectivity assays and Western blotting.

Based on multiple experiments conducted by inventors, the level of virus production in the cells overexpressing TULA was ~3 to 4-fold lower than that in vector control cells. Similarly, the effect of TULA-2 overexpression on virus production was ~4 to 5-fold.

It was also discovered that loss of TULA enhances virus production.

Considering that results obtained using protein overexpression require validation by depletion of endogenous proteins, inventors examined whether the depletion of TULA proteins affects virus production in the system. TULA-2 was silenced in 293T cells using a set of specific siRNA (Dharmacon). TULA-2 was selected for this experiment because (a) 293T cells do not express TULA (see [2]) and (b) the effects of TULA and TULA-2 on virus production are similar (FIG. 2).

Figure 3A:
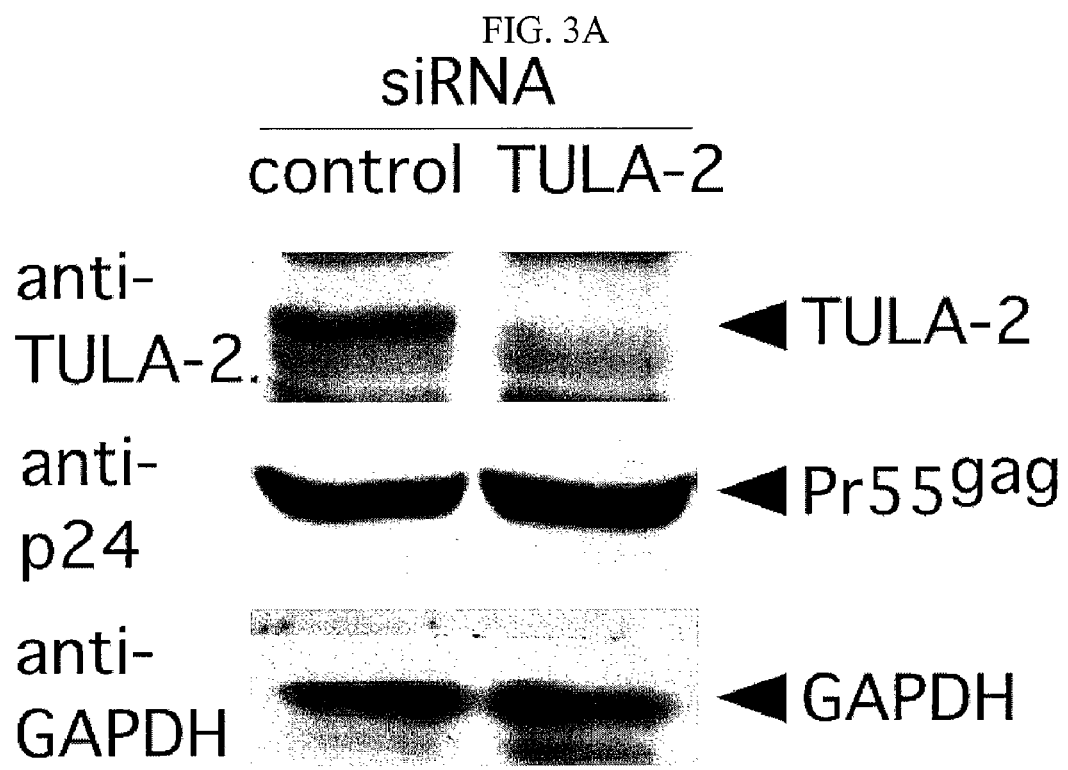
FIGS. 3A-3B demonstrate the effect of TULA-2 depletion on the production of HIV-1-based lentivirus. 293T cells were co-transfected with the pool of TULA-2 specific siRNA twice with a 24-hour interval between transfections. The plasmids required for the production of HIV-1 based VSVG-pseudotyped lentivirus were transfected with the second batch of siRNA.
Figure 3B:
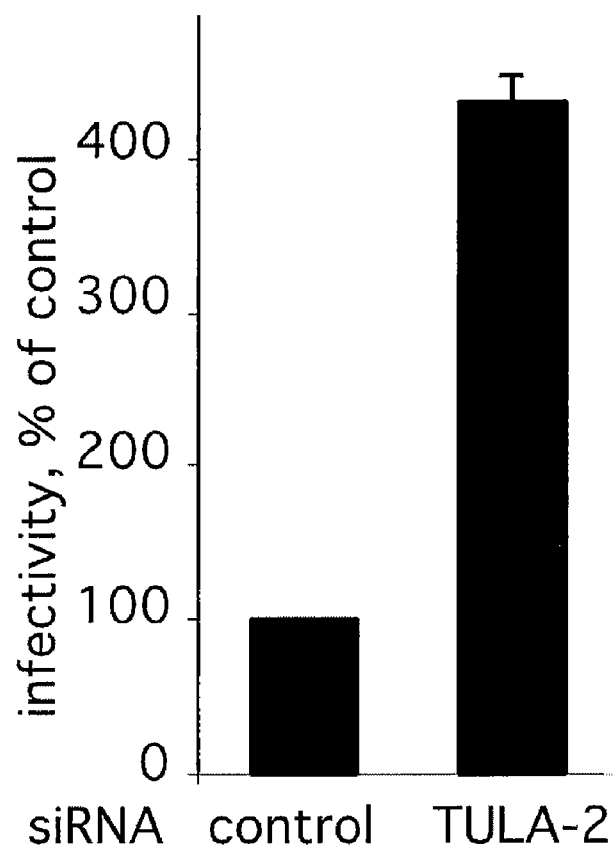

Cells were transfected with a pool of TULA-2 specific siRNAs and re-transfected 24 hours later with a mixture of the same siRNAs and the plasmids required for production of viral particles. The treatment with TULA-2 siRNA completely suppressed TULA-2 expression in virus-producing 293T cells (FIG. 3A) and dramatically upregulated virus production (FIG. 3B). Therefore, inventors demonstrated that both overexpression and silencing of TULA proteins exert a significant effect on HIV-1 biogenesis; overexpression decreases HIV-1 production, while silencing increases it. These findings demonstrate that inhibition of HIV-1 is a physiological function of endogenous TULA.

Mechanisms of the Effect of TULA

Considering that ubiquitylation of Gag is involved in HIV-1 biogenesis [5, 6] [15,16] and that TULA binds to the ubquitin-protein ligase c-Cbl [4], it is conceivable that TULA acts by sequestering c-Cbl, thus preventing ubiquitylation of relevant targets in this system. A recent study also hinted that c-Cbl may act as a negative regulator of signaling required for HIV-1 biogenesis [17]. Therefore, inventors assessed the effect of c-Cbl overexpression on the viral titer in the above described system. These experiments indicated that neither wild-type c-Cbl nor its ubiquitylation-deficient mutant C381A significantly influences the viral titer (data not shown), thus demonstrating that the observed effect of TULA on HIV-1 production is independent of c-Cbl.

Figure 2C:
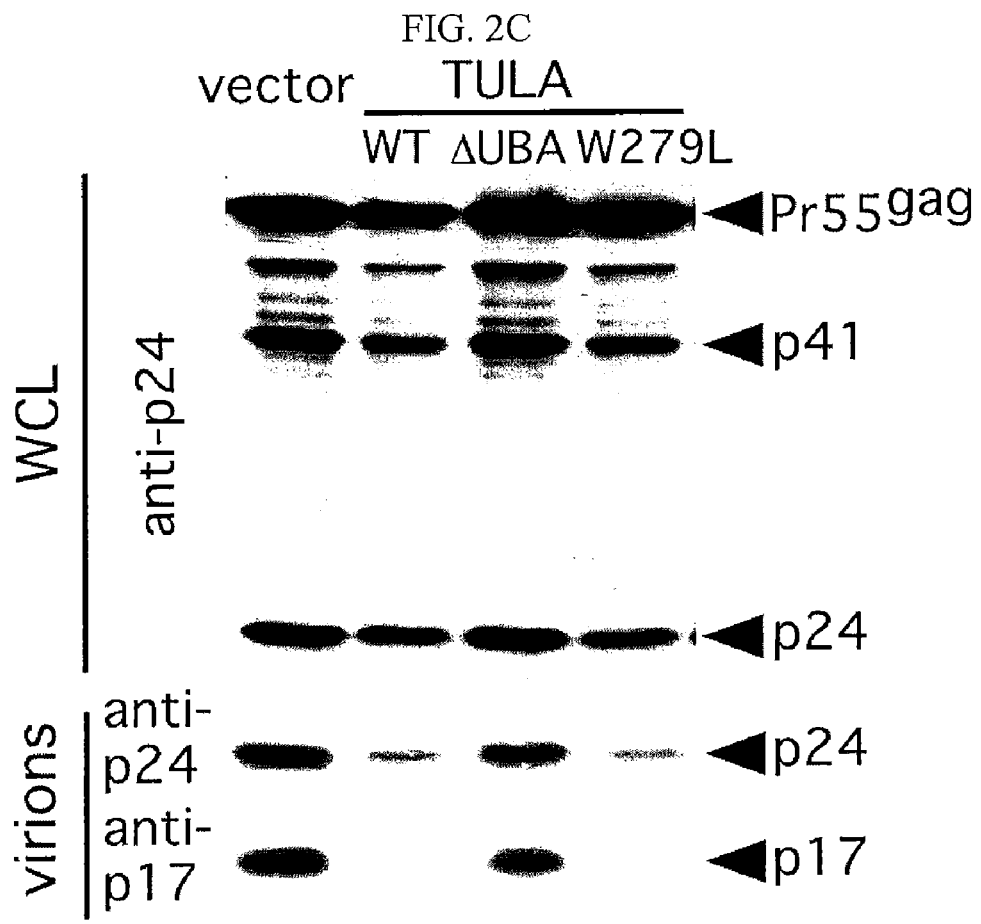
Figure 2D:
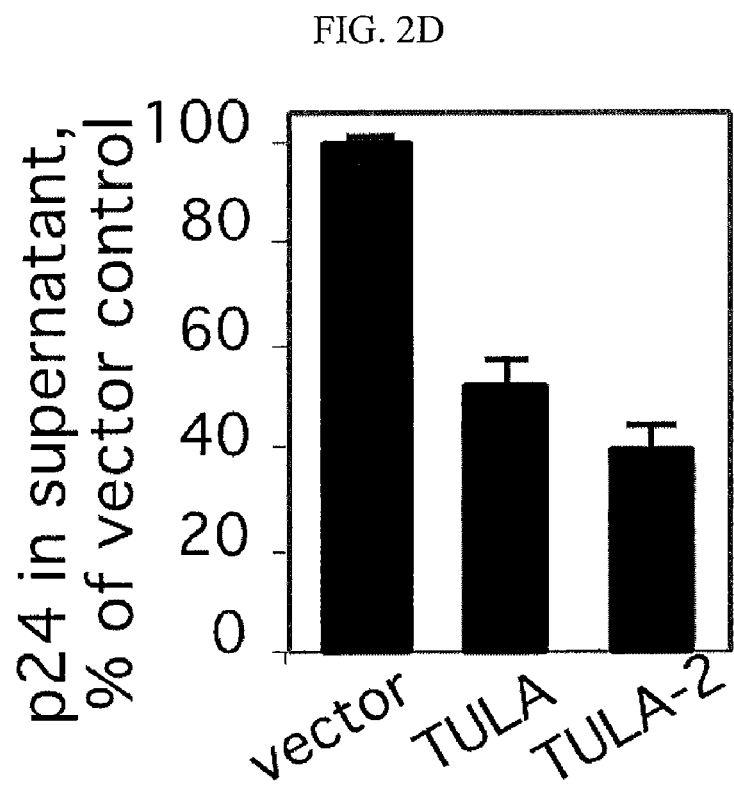

Since TULA binds to HP68/RLI which is a host factor for HIV-1 capsid assembly and therefore may perturb normal interactions between HIV-1 Gag and HP68/RLI [39], inventors believe that TULA may affect HIV-1 biogenesis by inhibiting virus maturation through the interference with capsid assembly. However, the recently proposed role of HP68/RLI in translation [18-21] made it conceivable that TULA acts on HIV-1 biogenesis by interfering with HIV-1 protein expression. To test this possibility, inventors analyzed the level of HIV-1 Gag in 293T cells expressing Gag alone or co-expressing Gag with HP68/RLI and/or TULA. The results of these experiments indicated that TULA has a very modest, if any, effect on the total level of Gag (FIG. 4, see also FIG. 2C). Also, TULA did not reduce the protein level of HP68/RLI (FIG. 4).

Interestingly, co-expression of TULA with Gag resulted in the pattern of Gag processing that is typical for the impairment of late steps of HIV-1 maturation, which is characterized by the appearance of the p25 band [22-24]. No p25 or very little of it was seen in the absence of TULA (FIG. 4) or in the presence of TULA mutants incapable of inhibiting HIV-1 biogenesis (data not shown). These findings together with the lack of a substantial effect of TULA proteins on the expression level of Gag suggested that TULA acts on HIV-1 biogenesis at the level of late steps of HIV-1 maturation.

Inventors believe that binding of TULA to HP68/RLI impairs Gag-HP68/RLI interaction by binding to HP68/RLI, since TULA may compete with HP68/RLI for Gag. To test this hypothesis, inventors co-expressed Gag, HP68/RLI and TULA in several combinations, immunoprecipitated Gag and detected co-immunoprecipitated HP68/RLI using Western blotting, adjusting its amount for the amount of immunoprecipitated Pr55$^{Gag}$, a form of Gag to which HP68/RLI binds [39]. In parallel, expression levels of all transfected proteins were analyzed using Western blotting. The experiment shown in FIG. 5A indicates that the amount of HP68/RLI co-immunoprecipitating with Gag is significantly decreased in the presence of TULA.

Therefore, these results indicated that the inhibitory effect of TULA on HIV-1 biogenesis correlates with a decrease in binding of HIV-1 Gag to HP68/RLI (FIG. 5A). Since the UBA domain of TULA is essential for the TULA-dependent inhibition of HIV-1 biogenesis (FIGS. 2A,C), inventors believe that this domain is essential for disrupting the interaction of HIV-1 Gag and HP68/RLI, probably by binding to ubiquitylated Gag.

Figure 5B:
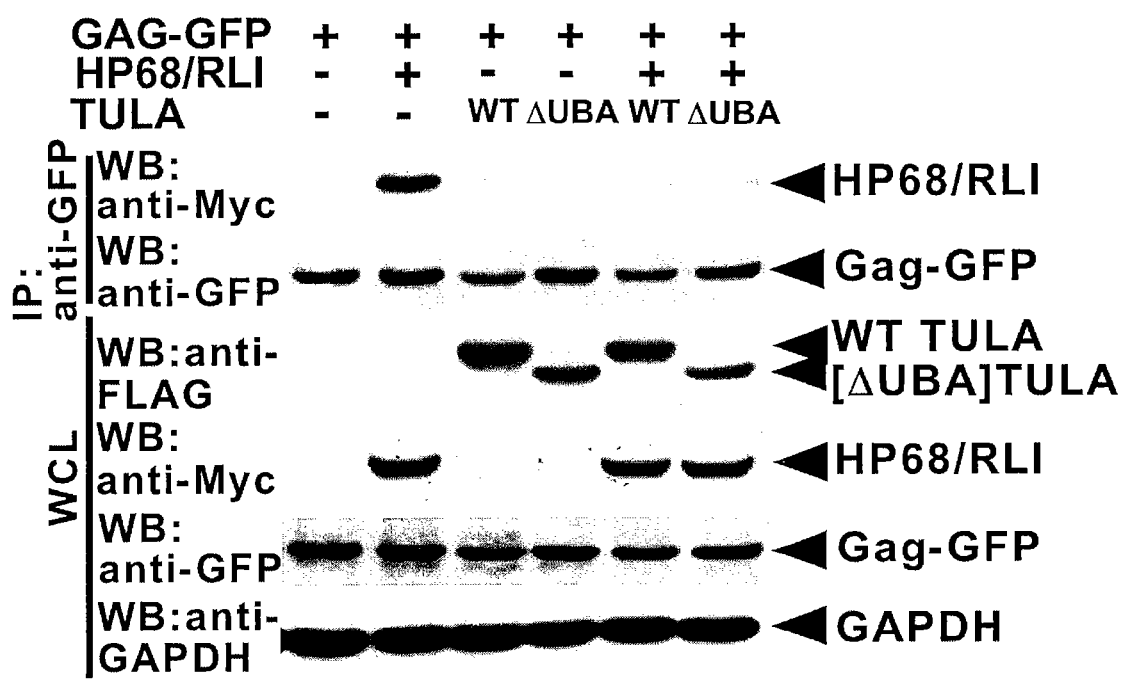

To test this hypothesis, the effect of [ΔUBA]TULA on co-immunoprecipitation of Gag and HP68/RLI were analyzed. [ΔUBA]TULA was shown to dramatically disrupt Gag-HP68/RLI binding (FIG. 5B). Taken together with the inability of [ΔUBA]TULA to inhibit HIV-1 biogenesis (FIG. 2), these findings indicate that the disruption of Gag-HP68/RLI binding alone is not sufficient for the inhibition of HIV-1 biogenesis by TULA.

Protein ubiquitylation appears to be involved in HIV-1 biogenesis (for example, [15,16]). Trafficking of Gag may be the major mechanism mediating the effect of ubiquitylation on HIV-1 biogenesis [25-27]. It has been shown that the UBA domain of TULA binds well to ubiquitin and that TULA can regulate some ubiquitylation-dependent events, such as endocytosis of ubiquitylated PTKs [2, 4]. Hence, inventors believe that the effect of TULA on HIV-1 biogenesis may be due to the TULA-dependent inhibition of the intracellular traffic of HIV-1 Gag. This effect of TULA, if occurs, should manifest itself in a change in the intracellular localization of HIV-1 Gag in the cells of overexpressing TULA. To test this hypothesis, inventors utilized GFP-fused Gag, a fluorescent protein that is fully capable of producing HIV-1 viral particles [28], for tracking HIV-1 Gag localization. Gag-GFP showed punctate localization, primarily to the plasma membrane proximal area, in the absence of TULA co-expression. Co-expression of wild-type TULA with Gag-GFP profoundly modified Gag-GFP localization; Gag-GFP accumulated in large membrane compartments, primarily in the perinuclear area. (These compartments are likely to be related to multi-vesicular bodies.) In contrast, [ΔUBA]TULA did not affect Gag-GFP localization (FIG. 6).

TULA clearly affects Gag-GFP localization, which is indicative of Gag intracellular trafficking, in a UBA-dependent fashion. The same dependence on the UBA domain is characteristic for the inhibitory effect of TULA on HIV-1 biogenesis (FIG. 2).

The results presented herein indicate that TULA proteins are capable of inhibiting HIV-1 biogenesis, that this inhibition is likely to be a natural function of endogenous TULA proteins and that this inhibition is mediated by TULA's UBA domain, mostly likely by impairing the normal course of HIV-1 Gag trafficking.

Screening for Molecules Mimicking the Effect of TULA in Inhibiting Maturation of Retrovirus Molecules mimicking the effect of TULA in inhibiting maturation of retrovirus inhibit biogenesis of retrovirus as indicated by a decrease in the production of viral particles and modification of Gag localization in the cell which can be evaluated using immunofluorescence microscopy with anti-GAG immunostaining.

Once the fragments of TULA and/or TULA-2 responsible for its negative effect on HIV-1 biogenesis are mapped, peptides can be synthesized that correspond to yet shorter fragments of the functional domain of TULA and/or TULA-2 and assess their ability to inhibit HIV-1 biogenesis as described in Example 4. If their membrane permeability needs to be facilitated, these peptides will be modified with N- and/or C-terminal hydrophobic groups. The structure of active peptides can be used to design non-peptide molecules that resemble them structurally and functionally. Practical approaches in preparing peptidomimetic (non-peptide analogues) of biologically active peptides have been described in multiple published reports (see for example, ([31, 33, 34], reviewed in [30]).

Peptidomimetics may be of different chemical nature, and therefore examples of their synthesis are numerous and varied. For example, peptidomimetics containing squaryldiamide as a potential bioisostere replacement for guanidine that bind transactivation responsive RNA (TAR) of HIV-1 with high affinity have been synthesized Chi-Wan Lee, Hong Cao, Kozi Ichiyama and Tariq M. Rana. Design and synthesis of a novel peptidomimetic inhibitor of HIV-1 Tat-TAR interactions: Squaryldiamide as a new potential bioisostere of unsubstituted guanidine. Bioorganic & Medicinal Chemistry Letters, Volume 15, Issue 19, Pages 4243-4246. Synthesis of peptidomimetics that include spiro-pyrrolidone, spiro-morpholinone, mono-substituted pyrrolidine and 2-imidazolidinone groups that can serve as HIV protease inhibitors provides another example of this procedure (Wieslaw M. Kazmierski, Eric Furfine, Yolanda Gray-Nunez, Andrew Spaltenstein and Lois Wright. Potent inhibitors of the HIV-1 protease incorporating cyclic urea P1-P2 scaffold. Bioorganic & Medicinal Chemistry Letters, Volume 14, Issue 22, Pages 5685-5687).

Effect of oxadiazols, compounds dissimilar to TULA and, most likely, acting differently, on localization of fluorescently labeled HIV-1 was shown using immunosluorescence microscopy. Haffar O, Dubrovsky L, Lowe R, Berro R, Kashanchi F, Godden J, Vanpouille C, Bajorath J, Bukrinsky M. Oxadiazols: a new class of rationally designed anti-human immunodeficiency virus compounds targeting the nuclear localization signal of the viral matrix protein. J. Virol. 2005 October; 79(20):13028-36. PMID: 16189005. Immunofluorescence microscopy was also used to assess the effect of cyclohexamide, a protein translation inhibitor, on Gag-GFP localization (Perlman and Resh, 2006).

It will be understood by those skilled in the art that not all of the atoms present in a significant contact residue need be present in a competitive binding agent. In fact, it is only those few atoms that shape the loops and actually form important contacts that are likely to be important for activity. Those skilled in the art will be able to identify these important atoms based on the structure model of the invention, which can be constructed using the structural data herein.

The design of compounds that bind to Gag-GFP region according to this invention generally involves the following consideration of two factors. First, the compound must be capable of either competing for binding with an immunogenic TULA protein; or physically and structurally associating with the ubiqutin domain. Non-covalent molecular interactions important in this association include hydrogen bonding, van der Waals interactions, hydrophobic interactions and electrostatic interactions. The compounds mimicking TULA should resemble the site (fragment, domain) of TULA that exerts the inhibitory effect, e.g., UBA. This site does not have to bind to Gag, it may work by binding to cellular proteins that affect Gag localization and HIV-1 biogenesis. That site of TULA may bind to Gag.

The compound must be able to assume a conformation that allows it to interact with the binding pocket. Although certain portions of the compound will not directly participate in these associations, those portions may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several interacting chemical moieties.

Computer-based methods of analysis fall into two broad classes: database methods and de novo design methods. In database methods the compound of interest is compared to all compounds present in a database of chemical structures and compounds whose structure is in some way similar to the compound of interest are identified. The structures in the database are based on either experimental data, generated by NMR or x-ray crystallography, or modeled three-dimensional structures based on two-dimensional data. In de novo design methods, models of compounds whose structure is in some way similar to the compound of interest are generated by a computer program using information derived from known structures, e.g. data generated by x-ray crystallography and/or theoretical rules. Such design methods can build a compound having a desired structure in either an atom-by-atom manner or by assembling stored small molecular fragments. Selected fragments or chemical entities may then be positioned in a variety of orientations, or docked, within the interacting surface of the RNA. Docking may be accomplished using software such as Quanta (Molecular Simulations, San Diego, Calif.) and Sybyl, followed by energy minimization and molecular dynamics with standard molecular mechanics force fields, such as CHARMM and AMBER.

Specialized computer programs may also assist in the process of selecting fragments or chemical entities. These include: SmoG, GRID (Goodford (1985) J. Med. Chem., 28, pp. 849 857; Oxford University, Oxford, UK; MCSS (Miranker et al. (1991) Proteins: Structure, Function and Genetics, 11, pp. 29 34; Molecular Simulations, San Diego, Calif.); AUTODOCK (Goodsell et al., (1990) Proteins: Structure, Function, and Genetics, 8, pp. 195 202; Scripps Research Institute, La Jolla, Calif.); and DOCK (Kuntz et al. (1982) J. Mol. Biol., 161:269 288; University of California, San Francisco, Calif.)

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates. Useful programs to aid one of skill in the art in connecting the individual chemical entities or fragments include: CAVEAT (Bartlett et al., (1989) In Molecular Recognition in Chemical and Biological Problems", Special Pub., Royal Chem. Soc., 78, pp. 182 196; University of California, Berkeley, Calif.); 3D Database systems such as MACCS-3D (MDL Information Systems, San Leandro, Calif.); and HOOK (available from Molecular Simulations, San Diego, Calif.).

Other molecular modeling techniques may also be employed in accordance with this invention. See, e.g., N. C. Cohen et al., "Molecular Modeling Software and Methods for Medicinal Chemistry, J. Med. Chem., 33, pp. 883 894 (1990). See also, M. A. Navia et al., "The Use of Structural Information in Drug Design", Current Opinions in Structural Biology, 2, pp. 202 210 (1992).

Once the binding entity has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit by the same computer methods described above.

Another approach made possible and enabled by this invention, is the computational screening of small molecule databases. In this screening, the quality of fit of such entities to the binding site may be judged either by shape complementarity or by estimated interaction energy. Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential side effects due to unwanted interactions with other proteins.

Compounds of interest can be systematically modified by computer modeling programs until one or more promising potential analogs are identified. In addition systematic modification of selected analogs can then be systematically modified by computer modeling programs until one or more potential analogs are identified. Alternatively a potential modulator could be obtained by initially screening a random peptide library, for example one produced by recombinant bacteriophage. A peptide selected in this manner would then be systematically modified by computer modeling programs as described above, and then treated analogously to a structural analog.

Once a potential modulator/inhibitor is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential modulator may be synthesized de novo. The de novo synthesis of one or even a relatively small group of specific compounds is reasonable in the art of drug design.

The success of both database and de novo methods in identifying compounds with activities similar to the compound of interest depends on the identification of the functionally relevant portion of the compound of interest. For drugs, the functionally relevant portion may be referred to as a pharmacophore, i.e. an arrangement of structural features and functional groups important for biological activity. Not all identified compounds having the desired pharmacophore will act as a modulator of inflammation. The actual activity can be finally determined only by measuring the activity of the compound in relevant biological assays. However, the methods of the invention are extremely valuable because they can be used to greatly reduce the number of compounds that must be tested to identify an actual inhibitor. In order to determine the biological activity of a candidate pharmacophore it is preferable to measure biological activity at several concentrations of candidate compound. The activity at a given concentration of candidate compound can be tested using, for example, single-round infectivity, production of viral particles, or p24 in cell culture supernatant. In addition, the results indicating that TULA perturbs localization of Gag in a specific fashion (FIG. 6), immunofluorescence microscopy can also be used to assess the effect of a particular compound on the distribution of Gag in the cell. General principles on which these methods are based have been described in detail, and kits are available for some of them (for example, for the measurement of p24 in supernatant). Brief outlines of these techniques can are as follows.

Single-round infectivity and quantification of virus particles using Western blotting of p24: cells (such as 293T) are grown to be ~30% confluent on the day of transfection, and purified plasmids required for lentivirus production are transfected into these cells using calcium phosphate or another appropriate transfection agent. Virus-containing supernatants are harvested and filtered through a 0.45-µm filter when appropriate (Hasham and Tsygankov, 2004). Virus production is assessed using a single-round infectivity assay and biochemical analysis of purified virions. The single-round infectivity assay is based on flow-cytometric enumeration of target cells infected with a replication-incompetent virus encoding for GFP (Alroy et al., 2005). For this purpose, filtered viral supernatants are added to Jurkat or other appropriate cells in 24-well plates ($2 \times 10^5$ cells/0.5 ml of medium per sample) in the presence of 8 µg/ml polybrene, and cells are spin-inoculated at 800×g for 90 min at 32° C. Jurkat cells are then analyzed using flow cytometry 2 days after spin-inoculation. The percentage of infected (GFP+) cells typically shows the linear dependence on the volume of supernatant in the range from 2 to 100 µl (corresponding to the multiplicity of infection from ~0.01 to ~0.5). To assess virus production using Western blotting, viral supernatant is centrifuged through a 20% sucrose cushion at 50,000×g for 90 min at +4° C., the pellet is lysed in SDS-containing or other appropriate buffer, and the amount of p24 in this sample is determined using standard Western blotting procedures.

Measurement of p24 in cell supernatant: Virus production by infected cells can also be evaluated by measuring p24, a viral protein, in cell supernatant. This can be achieved using multiple methods, including Western blotting, radioimmunoprecipitation assay (RIPA), enzyme-linked immunoassay (ELISA), etc. Antigen-capture ELISA is a convenient technique for which multiple kits are available (for example, from SAIC of Frederick, Md., or from ZeptoMetrix, Buffalo, N.Y.). In these assays, p24 is captured by a plate-immobilized anti-p24 antibody and detected using another anti-p24 antibody (for example, biotinylated) followed by secondary reagent (for example, streptavidin) conjugated with an enzyme (such as peroxidase). The amount of p24 in specimens is quantified using a standard curve of purified HIV-1 p24 antigen.

Immunofluorescence microscopy: To obtain immunofluorescence images, cells (such as HeLa) are transfected with a plasmid encoding for wild-type Gag or Gag conjugated with a fluorescent protein (such as GFP) using any appropriate transfection reagent. Later, cells are harvested and seeded on glass coverslips. (It is also possible to transfect cells directly on coverslips. Also, coverslips may be subjected to various treatments to improve cell spreading, such as pre-coating with fibronectin.) The cells are then washed, fixed with formaldehyde in buffered balanced salt solution (PBS, HBSS), washed again and permeabilized with a detergent. The fixed cells can be analyzed directly, if they are transfected with Gag-GFP or a similar labeled Gag, or immunostained using anti-Gag antibodies following a standard procedure. The cells (immunostained or expressing fluorescently labeled Gag) are washed, and the coverslips are mounted onto a slide with anti-fade mounting solution. Cell images can be obtained using any, but preferably confocal, fluorescence microscope.

In each case, the compounds to be tested will be added to the virus-producing cells at several concentrations, and the effects of these compounds will be determine by comparing virus production and/or Gag localization in their presence to those in the absence of any compound (negative control) or in the presence of co-expressed TULA (positive control). The compounds exerting effects similar to those of TULA will be deemed to be biologically active.

In yet another aspect, the invention is a method of identifying a fragment of a TULA protein having antiretroviral activity for the modulating a disorder selected from the group consisting of viral infections, HIV infection, autoimmune disease, and cancer, the method comprising: (a) providing a cell infected with a retrovirus; (b) providing a test agent comprising the fragment of the TULA protein; (d) combining the cell infected with a retrovirus with the test agent; (e) measuring retrovirus production in the presence of the test agent; (f) measuring retrovirus production in a control sample having no test agent; and (g) comparing retrovirus production in the control sample with retrovirus production in the test sample to identify the fragment of the TULA protein having antiretroviral activity which modulates the disorder selected from the group consisting of viral infections, HIV infection, autoimmune disease, and cancer.

The invention will be illustrated in more detail with reference to the following Examples, but it should be understood that the present invention is not deemed to be limited thereto.

EXAMPLES

Example 1

Preparation of TULA and Fragments Thereof

JMC-D3 cells ($2 \times 10^9$) were lysed in 10 ml of TNLE buffer containing 50 mM Tris, 150 mM NaCl, 0.5 mM EDTA, 1%

NP-40, 10 mM NaF, 1 mM Na$_3$VO$_4$, 1 mM PMSF, 10 µg/ml leupeptin, and 10 µg/ml aprotinin (pH 7.4) on ice for 20 min. Lysate pre-cleared by centrifugation was mixed with 2 volumes of ice-cold start buffer (20 mM sodium phosphate, 0.2 M NaCl and 10 mM imidazole, pH 7.4) and loaded on a 5-ml HiTrap Ni$^{2+}$-chelation column (Amersham Pharmacia Biotech, Piscataway, N.J.). The column was washed with 30 or 40 ml of ice-cold start buffer, and then eluted with two 10-ml portions of ice-cold sodium phosphate/NaCl buffer containing, in succession, 0.1 M and 0.5 M imidazole. The 0.1 M-imidazole fraction containing the majority of c-Cbl was mixed with 1 ml of agarose-immobilized anti-c-Cbl (Santa Cruz Biotechnology, Santa Cruz, Calif.) at 4° C. for 30 min. The suspension was transferred into a 5-ml column (BioRad, Hercules, Calif.) and washed twice with 5 ml of ice-cold TBS with 0.1% NP-40 (pH 7.4). The antibody-bound material was eluted with 5 ml of 0.1 M glycine buffer (pH 3). All flow-through, wash and elution fractions collected in the course of this purification were analyzed using SDS-PAGE followed by silver (Silver Stain Plus, BioRad) or colloidal Coomassie (Colloidal Blue Stain, Invitrogen/Life Technologies, Carlsbad, Calif.) staining.

Protein bands specific to the glycine elution lane, as well as two major bands of 53 and 63 kDa that were present in both the elution and the second wash lanes and a 48-kDa band that was present in the second, but not the first wash lane, were excised and digested with trypsin as previously reported [38]. The resulting digests were analyzed by on-line LC-ES MS/MS using reverse phase capillary HPLC (C18, 75 µm×10 cm, 3 µm particles) coupled to an LCQ Deca ion trap mass spectrometer equipped with an in-house-built nanoLC interface. Tryptic peptides were sequenced in a data-dependent manner as they were eluted from the HPLC [32]. Uninterpreted spectra were searched against a non-redundant protein database using Mascot [35].

One of the c-Cbl-associated proteins was TULA, which was identified using the following peptides: SEQ. ID. NO.: 9 [MYTFSKATDKHSR], SEQ. ID. NO.: 10 [IAGDALLDSGIR], SEQ. ID. NO.: 11 [TLEQLAR], and SEQ. ID. NO.: 12 [VDQIFGK]. The DNA sequence encoding for TULA-2 (SEQ ID NO: 5) was found through a homology search using PubMed. Examples of sequences deposited in the GenBank that contained a homologue of TULA include NP_116262, BAC11468.

Following identification, TULA and TULA-2 as well as several of their fragments were purified as recombinant GST-fusion proteins. Preparation of plasmids encoding these proteins will be described in Example 3. The method used for their purification was identical in all cases. Bacterial (*E. coli*) cells were transformed with an expression plasmid and grown in appropriate media until A$_{600}$ reached 0.6. GST-protein expression was induced with 0.1 mM IPTG for 3 hours. Bacterial cells were centrifuged, frozen and kept frozen until purification. When used for purification, cells were thawed in sonication buffer (PBS, pH 7.4, containing aprotinin/leupeptin 10 ug/ml each, PMSF 1 mM, and 0.1 mg/ml soybean trypsin inhibitor) and sonicated on ice. Lysates were centrifuged, and their supernatants were collected and mixed with suspension of Glutathione-Sepharose. Triton X-100 was added to the supernatants to a final concentration of 1%. Supernatants were rotated with Glutathione-Sepharose beads at +4° C. for ~1 hour. The beads were separated by centrifugation and washed three times in PBS containing 1% Triton X-100 and then three times in PBS. To elute proteins, beads were mixed with 10 mM glutathione in 50 mM Tris/HCl, pH 8, and rotated for 15 m in. Beads were removed by centrifugation, and the protein-containing supernatant was collected and stored.

Example 2

Preparation of TULA Containing Plasmids

The first strand of TULA cDNA was synthesized from total JMC-D3 RNA using AMV reverse transcriptase (Promega, Madison, Wis.) and then amplified using Advantage-HF2 PCR kit (Clontech, Palo Alto, Calif.) with TULA-specific primers: 5'-GGC AGG AAG AGA TGG CAG CG-3' (sense) (SEQ. ID. NO.: 13) and 5'-GAG GTT ATG ACA ACA TCA CCG TGG-3' (antisense) (SEQ. ID. NO.: 14). The PCR product was cloned into pcDNA3.1/V5-His TOPO vector (Invitrogen/Life Technologies). Positive clones were selected and sequenced on both strands. The obtained sequences of TULA were submitted to GenBank under accession numbers AF520809 (long) and AF521702 (short). The TULA-2 plasmid was prepared in the same fashion.

Example 3

Preparation of TULA Expressing Vectors

The KpnI/PmeI fragment of TULA cDNA from pcDNA3.1/V5-His was subcloned into KpnI/SmaI sites of pAlterMAX (Promega) or BamHI/SmaI sites of pGEX2T (Amersham Pharmacia Biotech). Mutations were introduced into TULA (to generate [ΔUBA] TULA and [W279L]TULA mutant forms) using Pfu Turbo DNA polymerase (Stratagene, La Jolla, Calif.) as described [37]. The primers for UBA deletion were 5'-TGC AAT GAC CCT TCC CTA GAC GAC ATC CCC CA-3' (sense) (SEQ. ID. NO.: 15) and 5'-GCG GCT CTT GAG CTT GTT GGA GAC CTT GGC GTA GA-3' (antisense) (SEQ. ID. NO.: 16). The primers for W279L substitution were 5'-TCA CAG CGG ACG GGC TGC CGG GGC T-3' (sense) (SEQ. ID. NO.: 17) and 5'-GAT CCC AAT CAC CAG GCC CTC GCT GGT GGT C-3' (antisense) (SEQ. ID. NO.: 18). All mutations were verified by sequencing of both strands of DNA products. Expression plasmids for TULA-2 were prepared in the identical fashion.

Example 4

Obtaining Minimal Fragment(s) of TULA Capable of the Inhibitory Effect on HIV-1 Biogenesis The experiments focused on the search for minimal fragments will recapitulate the studies of the effects of full-length TULA and TULA-2 as described herein. These experiments will be described here using the UBA domain as an example. Other fragments will be examined using the same approach.

First, the UBA domain of either TULA or TULA-2 will be coexpressed in 293T cells with the three-plasmid system required for production of recombinant HIV-1 and this production will be measured using single-cycle infectivity, immunoblotting of p24 and p17 in virions, and ELISA of p24 in cellular supernatants as shown in FIGS. 2 and 3. If TULA and/or TULA-2 UBA specifically inhibit HIV-1 biogenesis, the effect of transmembrane delivery of this UBA domain on HIV-1 biogenesis will be examined. We will produce this domain as a recombinant protein (see Example 1) and transfect it into 293T cells using Chariot reagent (Active Motif) as described in our previous study [36]. If Chariot-facilitated transfection of UBA inhibits HIV-1 biogenesis, we will generate TULA and/or TULA-2 UBA fusions to membrane-shuttling peptides, such as the *Drosophila* protein Antennapedia, the HIV-1 protein Tat or VP22 from HSV-1, and evaluate their effect on HIV-1 biogenesis. These fusions will serve as prototypes of TULA-based anti-HIV/AIDS therapeutic tools. The small size of a UBA domain (~40 amino acids) favors the use of this approach.

Other fragments of TULA and TULA-2 will be analyzed in the same fashion, i.e., first expressed in HIV-producing cells and, if they exert a significant effect on HIV-1 biogenesis, then transfected (as proteins) to HIV-producing cells. If a particular fragment is highly effective in suppressing HIV-1 biogenesis, it will be fused to membrane-permeating peptides, and its effects will be assessed further.

Example 5

The use of TULA-based therapeutic tools may be illustrated using the following prophetic examples.

Example 5A

The peptide consisting of TULA UBA (or another active fragment of TULA) and a membrane-permeable fragment of one of the proteins listed in Example 4 will be made in bacteria, purified and administered (e.g., injected/infused intravenously) to an HIV-positive patient at a dose having a therapeutic effect in the absence of significant side effects. The peptide will cross the biological membrane and inhibit HIV-1 biogenesis in HIV-1-infected cells. This treatment will therefore prevent further spread of HIV-1 and infection of healthy cells. This drug is likely to be administered in a combination with other anti-HIV-1 drugs and pharmaceutically acceptable carriers. Since the TULA-based drugs will affect a step in the HIV-1 life cycle that is not affected by other drugs, their combinatory use will be especially potent.

Example 5B

The UBA domain of TULA (or another active fragment of this protein) may be delivered using one of targeted drug delivery techniques. For instance, this peptide may be delivered inside liposomes (or similar particles) coated with anti-CD4 antibody. These particles will preferentially target cells having the CD4 membrane marker on their surface, i.e., T-helpers and monocytes/macrophages, cells that represent main targets of HIV-1. It is also possible to coat the peptide-carrying liposomes with recombinant CD4. These liposomes will target cells that express HIV-1 gp120 on their surface, i.e. HIV-1 infected cells. Administration of drug-carrying liposomes will be conducted using, for example, intravenous injection/infusion. This approach may increase efficacy of the TULA-based drugs and reduce their side effects if any. It will also abolish the need for a membrane-permeable peptide fused to the active TULA peptide.

Example 5C

Treatment with TULA-based peptide drugs may also be carried out ex vivo. In this case, while blood cells of HIV-1-positive patients will be isolated, treated with TULA-based drugs in vitro and re-infused to the patient. This approach may be used to reduce side effects of these drugs in cases when these effects will be substantial. In all examples (5A-C), active fragments of TULA, such as UBA, will enter HIV-1 infected cells and block maturation of HIV-1, thus preventing infection of healthy cells.

While the invention has been described in detail and with reference to specific examples thereof, it will be apparent to one skilled in the art that various changes and modifications can be made therein without departing from the spirit and scope thereof.

REFERENCES

1. Wattenhofer, M., Shibuya, K., Kudoh, J., Lyle, R., Michaud, J., Rossier, C., Kawasaki, K., Asakawa, S., Minoshima, S., Berry, A., Bonne-Tamir, B., Shimizu, N., Antonarakis, S. E., and Scott, H. S. (2001). Isolation and characterization of the UBASH3A gene on 21q22.3 encoding a potential nuclear protein with a novel combination of domains. *Hum Genet* 108, 140-7.
2. Feshchenko, E. A., Smirnova, E. V., Swaminathan, G., Teckchandani, A. M., Agrawal, R., Band, H., Zhang, X., Annan, R. S., Carr, S. A., and Tsygankov, A. Y. (2004). TULA: an SH3- and UBA-containing protein that binds to c-Cbl and ubiquitin. *Oncogene* 23, 4690-706.
3. Carpino, N., Turner, S., Mekala, D., Takahashi, Y., Zang, H., Geiger, T. L., Doherty, P., and Ihle, J. N. (2004). Regulation of ZAP-70 activation and TCR signaling by two related proteins, Sts-1 and Sts-2. *Immunity* 20, 37-46.
4. Kowanetz, K., Crosetto, N., Haglund, K., Schmidt, M. H., Heldin, C. H., and Dikic, I. (2004). Suppressors of T-cell receptor signaling Sts-1 and Sts-2 bind to Cbl and inhibit endocytosis of receptor tyrosine kinases. *J Biol Chem* 279, 32786-95.
5. Carpino, N., Kobayashi, R., Zang, H., Takahashi, Y., Jou, S. T., Feng, J., Nakajima, H., and Ihle, J. N. (2002). Identification, cDNA cloning, and targeted deletion of p70, a novel, ubiquitously expressed SH3 domain-containing protein. *Mol Cell Biol* 22, 7491-500.
6. Shindo, K., Takaori-Kondo, A., Kobayashi, M., Abudu, A., Fukunaga, K., and Uchiyama, T. (2003). The enzymatic activity of CEM15/Apobec-3G is essential for the regulation of the infectivity of HIV-1 virion but not a sole determinant of its antiviral activity. *J Biol Chem* 278, 44412-6.
7. Mangeat, B., Turelli, P., Caron, G., Friedli, M., Perrin, L., and Trono, D. (2003). Broad antiretroviral defense by human APOBEC3G through lethal editing of nascent reverse transcripts. *Nature* 424, 99-103.
8. Bishop, K. N., Holmes, R. K., and Malim, M. H. (2006). Antiviral Potency of APOBEC Proteins Does Not Correlate with Cytidine Deamination. *J Virol* 80, 8450-8.
9. Yap, M. W., Nisole, S., Lynch, C., and Stoye, J. P. (2004). Trim5alpha protein restricts both HIV-1 and murine leukemia virus. *Proc Natl Acad Sci USA* 101, 10786-91.
10. Stremlau, M., Perron, M., Lee, M., Li, Y., Song, B., Javanbakht, H., Diaz-Griffero, F., Anderson, D. J., Sundquist, W. I., and Sodroski, J. (2006). From the Cover: Specific recognition and accelerated uncoating of retroviral capsids by the TRIM5 {alpha} restriction factor. *Proc Natl Acad Sci USA* 103, 5514-9.
11. Carlson, K. A., Leisman, G., Limoges, J., Pohlman, G. D., Horiba, M., Buescher, J., Gendelman, H. E., and Ikezu, T. (2004). Molecular characterization of a putative antiretroviral transcriptional factor, OTK18. *J Immunol* 172, 381-91.
12. Alroy, I., Tuvia, S., Greener, T., Gordon, D., Barr, H. M., Taglicht, D., Mandil-Levin, R., Ben-Avraham, D., Konforty, D., Nir, A., Levius, O., Bicoviski, V., Dori, M., Cohen, S., Yaar, L., Erez, O., Propheta-Meiran, O., Koskas, M., Caspi-Bachar, E., Alchanati, I., Sela-Brown, A., Moskowitz, H., Tessmer, U., Schubert, U., and Reiss, Y. (2005). The trans-Golgi network-associated human ubiquitin-protein ligase POSH is essential for HIV type 1 production. *Proc Natl Acad Sci USA* 102, 1478-83.
13. Bolton, D. L., Hahn, B. I., Park, E. A., Lehnhoff, L. L., Hornung, F., and Lenardo, M. J. (2002). Death of CD4(+) T-cell lines caused by human immunodeficiency virus type 1 does not depend on caspases or apoptosis. *J Virol* 76, 5094-107.
14. Lenardo, M. J., Angleman, S. B., Bounkeua, V., Dimas, J., Duvall, M. G., Graubard, M. B., Hornung, F., Selkirk, M. C., Speirs, C. K., Trageser, C., Orenstein, J. O., and Bolton, D. L. (2002). Cytopathic killing of peripheral blood CD4 (+) T lymphocytes by human immunodeficiency virus type 1 appears necrotic rather than apoptotic and does not require env. *J Virol* 76, 5082-93.
15. Schubert, U., Ott, D. E., Chertova, E. N., Welker, R., Tessmer, U., Princiotta, M. F., Bennink, J. R., Krausslich, H. G., and Yewdell, J. W. (2000). Proteasome inhibition interferes with gag polyprotein processing, release, and maturation of HIV-1 and HIV-2. *Proc Natl Acad Sci USA* 97, 13057-62.
16. Gottwein, E., and Krausslich, H. G. (2005). Analysis of human immunodeficiency virus type 1 Gag ubiquitination. *J Virol* 79, 9134-44.
17. Simmons, A., Gangadharan, B., Hodges, A., Sharrocks, K., Prabhakar, S., Garcia, A., Dwek, R., Zitzmann, N., and McMichael, A. (2005). Nef-Mediated Lipid Raft Exclusion of UbcH7 Inhibits Cbl Activity in T Cells to Positively Regulate Signaling. *Immunity* 23, 621-34.
18. Estevez, A. M., Haile, S., Steinbuchel, M., Quijada, L., and Clayton, C. (2004). Effects of depletion and overexpression of the *Trypanosoma* brucei ribonuclease L inhibitor homologue. *Mol Biochem Parasitol* 133, 137-41.
19. Dong, J., Lai, R., Nielsen, K., Fekete, C. A., Qiu, H., and Hinnebusch, A. G. (2004). The essential ATP-binding cassette protein RLI1 functions in translation by promoting preinitiation complex assembly. *J Biol Chem* 279, 42157-68.
20. Kispal, G., Sipos, K., Lange, H., Fekete, Z., Bedekovics, T., Janaky, T., Bassler, J., Aguilar Netz, D. J., Balk, J., Rotte, C., and Lill, R. (2005). Biogenesis of cytosolic ribosomes requires the essential iron-sulphur protein Rli1p and mitochondria. *Embo J* 24, 589-98.
21. Yarunin, A., Panse, V. G., Petfalski, E., Dez, C., Tollervey, D., and Hurt, E. C. (2005). Functional link between ribosome formation and biogenesis of iron-sulfur proteins. *Embo J* 24, 580-8.
22. Gottlinger, H. G., Dorfman, T., Sodroski, J. G., and Haseltine, W. A. (1991). Effect of mutations affecting the p6 gag protein on human immunodeficiency virus particle release. *Proc Natl Acad Sci USA* 88, 3195-9.
23. Demirov, D. G., Orenstein, J. M., and Freed, E. O. (2002). The late domain of human immunodeficiency virus type 1 p6 promotes virus release in a cell type-dependent manner. *J Virol* 76, 105-17.
24. Martin-Serrano, J., and Bieniasz, P. D. (2003). A bipartite late-budding domain in human immunodeficiency virus type 1. *J Virol* 77, 12373-7.
25. Goff, A., Ehrlich, L. S., Cohen, S, N., and Carter, C. A. (2003). Tsg101 control of human immunodeficiency virus type 1 Gag trafficking and release. *J Virol* 77, 9173-82.
26. von Schwedler, U. K., Stuchell, M., Muller, B., Ward, D. M., Chung, H. Y., Morita, E., Wang, H. E., Davis, T., He, G. P., Cimbora, D. M., Scott, A., Krausslich, H. G., Kaplan, J., Morham, S. G., and Sundquist, W. I. (2003). The protein network of HIV budding. *Cell* 114, 701-13.
27. Perlman, M., and Resh, M. D. (2006). Identification of an Intracellular Trafficking and Assembly Pathway for HIV-1 Gag. *Traffic* 7, 731-45.
28. Sherer, N. M., Lehmann, M. J., Jimenez-Soto, L. F., Ingmundson, A., Horner, S. M., Cicchetti, G., Allen, P. G., Pypaert, M., Cunningham, J. M., and Mothes, W. (2003). Visualization of retroviral replication in living cells reveals budding into multivesicular bodies. *Traffic* 4, 785-801.
29. Zang, H. et al., (2003) The cytidine deaminase CEM15 induces hypermutation in newly synthesized HIV-1 DNA. Nature 424, 94-98.
30. Fletcher, S. & Hamilton, A. D. (2005). *Curr Opin Chem Biol,* 9, 632-8.
31. Fotsch, C., Smith, D. M., Adams, J. A., Cheetham, J., Croghan, M., Doherty, E. M., Hale, C., Jarosinski, M. A., Kelly, M. G., Norman, M. H., Tamayo, N. A., Xi, N. & Baumgartner, J. W. (2003). *Bioorg Med Chem Lett,* 13, 2337-40.
32. Gatlin, C. L., Kleemann, G. R., Hays, L. G., Link, A. J. & Yates, J. R., 3rd. (1998). *Anal Biochem,* 263, 93-101.
33. Jones, R. M., Boatman, P. D., Semple, G., Shin, Y. J. & Tamura, S. Y. (2003). *Curr Opin Pharmacol,* 3, 530-43.
34. Mavromoustakos, T., Moutevelis-Minakakis, P., Kokotos, C. G., Kontogianni, P., Politi, A., Zoumpoulakis, P., Findlay, J., Cox, A., Balmforth, A., Zoga, A. & Iliodromitis, E. (2006). *Bioorg Med Chem,* 14, 4353-60.
35. Perkins, D. N., Pappin, D. J., Creasy, D. M. & Cottrell, J. S. (1999). *Electrophoresis,* 20, 3551-67.
36. Teckchandani, A. M., Panetti, T. S. & Tsygankov, A. Y. (2005). *Exp Cell Res,* 307, 247-58.
37. Wang, J. & Wilkinson, M. F. (2001). *Biotechniques,* 31, 722-4.
38. Zhang, X., Herring, C. J., Romano, P. R., Szczepanowska, J., Brzeska, H., Hinnebusch, A. G. & Qin, J. (1998). *Anal Chem,* 70, 2050-9.
39. Zimmerman, C., Klein, K. C., Kiser, P. K., Singh, A. R., Firestein, B. L., Riba, S. C., and Lingappa, J. R. (2002). Identification of a host protein essential for assembly of immature HIV-1 capsids. *Nature* 415, 88-92.
40. Alroy, I., Tuvia, S., Greener, T., Gordon, D., Barr, H. M., Taglicht, D., Mandil-Levin, R., Ben-Avraham, D., Konforty, D., Nir, A., Levius, O., Bicoviski, V., Dori, M., Cohen, S., Yaar, L., Erez, O., Propheta-Meiran, O., Koskas, M., Caspi-Bachar, E., Alchanati, I., Sela-Brown, A., Moskowitz, H., Tessmer, U., Schubert, U. & Reiss, Y. (2005). *Proc Natl Acad Sci USA* 102, 1478-83.
41. Hasham, M. G. & Tsygankov, A. Y. (2004). *Virology* 320, 313-29.
42. Perlman, M. & Resh, M. D. (2006). *Traffic* 7, 731-45.

What is claimed is:

1. A method of inhibiting a retrovirus production, the method comprising administering a retrovirus inhibitor selected from the group consisting of at least one of a TULA protein, a UBA domain of a TULA protein, a polynucleotide encoding a TULA protein, and a polynucleotide encoding a UBA domain of a TULA protein, to a cell or a tissue infected by a retrovirus.

2. The method of claim 1, wherein the polynucleotide is at least one of SEQ ID NO: 1, SEQ ID NO: 3, SEQ ID NO: 5, and SEQ ID NO: 7.

3. The method of claim 1, wherein the retrovirus inhibitor is at least one of SEQ ID NO: 2, SEQ ID NO: 4, SEQ ID NO: 6, SEQ ID NO:8, and SEQ ID NO:19.

4. The method of claim 1, wherein said administering is achieved by expressing in the cell at least one of a retrovirus inhibitor selected from the group consisting of at least one of a TULA protein, a fragment of TULA containing a UBA domain, and a fragment of TULA consisting of a UBA domain.

5. The method of claim 1, wherein the retrovirus production is HIV-1 production.

* * * * *

SEQUENCE LISTING

<160> NUMBER OF SEQ ID NOS: 19

<210> SEQ ID NO 1
<211> LENGTH: 1986
<212> TYPE: DNA
<213> ORGANISM: Homo sapiens

```
<400> SEQUENCE: 1
atggcagcgg gggagacgca gctctacgcc aaggtctcca acaagctcaa gagccgcagc      60
agccctcgc tcctggagcc cctcctggcc atgggcttcc cggtgcacac cgcgctgaaa     120
gcgttggcag ccacggggag gaagacggcg gaggaggcct tggcctggct gcatgatcat     180
tgcaatgacc cttccctaga cgaccccatc ccccaggagt atgccctttt cctctgtcca     240
acggggcccc tgctggaaaa acttcaagag ttctggagag agagcaagcg ccagtgtgca     300
aagaacagag ctcatgaggt cttcccacac gtgacactct gtgacttctt cacgtgtgaa     360
gaccagaagg tggaatgcct gtacgaggcg ctgaagagag ctggagacag gctcctgggc     420
tccttcccca cggccgtgcc tctggctctc cactcctcca tcagctacct cggcttcttc     480
gtcagtggca gccccgcaga cgtcatccgg gaattcgcca tgaccttcgc cacggaagca     540
tctctcttag caggcacttc cgtttcccgc ttctggattt tcagccaggt gcctggacat     600
ggccctaacc tgaggctgag caatttaact agagcctcct tcgtgagcca ctacatcctt     660
caaaaatact gctccgtgaa gccttgcacc aaacagctgc atctgacctt ggcccacaag     720
ttctacccc accaccagag gacgctggag cagctggcca gagccatccc cctgggccac     780
agctgccagt ggaccgcagc actctactcc gagacatgc gctttgtgca ctaccagacc     840
ctgagagccc tattccagta caaacccag aacgtggatg agctgacgct aagtcctggt     900
gactacatct ttgtggaccc cacgcagcag gacgaagcca gcgagggctg ggtgattggg     960
atctcacagc ggacgggctg ccggggcttc ctgccggaaa actacacgga tcgagccagt    1020
gagtctgaca cgtgggtgaa gcacaggatg tacaccttca gtctagccac agacctgaac    1080
tccagaaagg atggtgaagc cagcagcaga tgcagcgggg aatttcttcc acaaacggca    1140
aggagtctta gcagcttaca ggccttgcag gctaccgttg caaggaagag cgtgctggtg    1200
gttcgccacg gggagagagt ggatcagatc ttcgggaagg catggctgca gcaatgctcc    1260
actcctgatg ggaaatacta caggccagac ctgaatttcc cctgcagtct gccaagacgg    1320
agtcgtggga tcaaagactt tgaaaacgat cccccattat catcgtgtgg cattttccag    1380
tccagaattg caggggacgc gctactggac agtggtatca gaatcagctc tgtgtttgcc    1440
tccccagccc tccgctgtgt gcagacggcc aaactcatcc tggaagaact caaactggag    1500
aaaaaaatca agatacgagt ggaacctgga atctttgaat ggacaaaatg ggaagctggc    1560
aaaaccaccc caaccctcat gagcctgaa gagctgaaag aggcaaattt caacattgac    1620
actgattaca ggcccgcgtt tcccctgtcc gccctcatgc cggccgagag ctaccaggag    1680
tacatggaca ggtgcacggc gagcatggtg caaatcgtca acacctgtcc acaggacacg    1740
ggtgtcatcc taattgtgag tcacggctcc actctgact cctgcacgcg ccactgctc    1800
gggctgccgc cccgggaatg tgggatttt gcccaactcg tgagaaagat cccttccctg    1860
ggcatgtgct ctgtgaagaa aaataaagag gaagggaaat gggagttggt gaacccaccg    1920
gtgaagaccc tgacccacgg ggcgaacgca gcatttaact ggaggaactg gatctcaggc    1980
aactga                                                                1986

<210> SEQ ID NO 2
<211> LENGTH: 623
<212> TYPE: PRT
<213> ORGANISM: Homo sapiens
```

```
<400> SEQUENCE: 2

Met Ala Ala Gly Glu Thr Gln Leu Tyr Ala Lys Val Ser Asn Lys Leu
 1               5                  10                  15

Lys Ser Arg Ser Ser Pro Ser Leu Leu Glu Pro Leu Leu Ala Met Gly
            20                  25                  30

Phe Pro Val His Thr Ala Leu Lys Ala Leu Ala Ala Thr Gly Arg Lys
             35                  40                  45

Thr Ala Glu Glu Ala Leu Ala Trp Leu His Asp His Cys Asn Asp Pro
     50                  55                  60

Ser Leu Asp Asp Pro Ile Pro Gln Glu Tyr Ala Leu Phe Leu Cys Pro
 65                  70                  75                  80

Thr Gly Pro Leu Leu Glu Lys Leu Gln Glu Phe Trp Arg Glu Ser Lys
                 85                  90                  95

Arg Gln Cys Ala Lys Asn Arg Ala His Glu Val Phe Pro His Val Thr
            100                 105                 110

Leu Cys Asp Phe Phe Thr Cys Glu Asp Gln Lys Val Glu Cys Leu Tyr
            115                 120                 125

Glu Ala Leu Lys Arg Ala Gly Asp Arg Leu Leu Gly Ser Phe Pro Thr
130                 135                 140

Ala Val Pro Leu Ala Leu His Ser Ser Ile Ser Tyr Leu Gly Phe Phe
145                 150                 155                 160

Val Ser Gly Ser Pro Ala Asp Val Ile Arg Glu Phe Ala Met Thr Phe
                165                 170                 175

Ala Thr Glu Ala Ser Leu Leu Ala Asp Cys Ser Val Lys Pro Cys Thr
            180                 185                 190

Lys Gln Leu His Leu Thr Leu Ala His Lys Phe Tyr Pro His His Gln
            195                 200                 205

Arg Thr Leu Glu Gln Leu Ala Arg Ala Ile Pro Leu Gly His Ser Cys
210                 215                 220

Gln Trp Thr Ala Ala Leu Tyr Ser Arg Asp Met Arg Phe Val His Tyr
225                 230                 235                 240

Gln Thr Leu Arg Ala Leu Phe Gln Tyr Lys Pro Gln Asn Val Asp Glu
                245                 250                 255

Leu Thr Leu Ser Pro Gly Asp Tyr Ile Phe Val Asp Pro Thr Gln Gln
            260                 265                 270

Asp Glu Ala Ser Glu Gly Trp Val Ile Gly Ile Ser Gln Arg Thr Gly
            275                 280                 285

Cys Arg Gly Phe Leu Pro Glu Asn Tyr Thr Arg Ala Ser Glu Ser
290                 295                 300

Asp Thr Trp Val Lys His Arg Met Tyr Thr Phe Ser Leu Ala Thr Asp
305                 310                 315                 320

Leu Asn Ser Arg Lys Asp Gly Glu Ala Ser Arg Cys Ser Gly Glu
                325                 330                 335

Phe Leu Pro Gln Thr Ala Arg Ser Leu Ser Ser Leu Gln Ala Leu Gln
            340                 345                 350

Ala Thr Val Ala Arg Lys Ser Val Leu Val Arg His Gly Glu Arg
            355                 360                 365

Val Asp Gln Ile Phe Gly Lys Ala Trp Leu Gln Cys Ser Thr Pro
370                 375                 380

Asp Gly Lys Tyr Tyr Arg Pro Asp Leu Asn Phe Pro Cys Ser Leu Pro
385                 390                 395                 400

Arg Arg Ser Arg Gly Ile Lys Asp Phe Glu Asn Asp Pro Pro Leu Ser
                405                 410                 415
```

```
Ser Cys Gly Ile Phe Gln Ser Arg Ile Ala Gly Asp Ala Leu Leu Asp
                420                 425                 430

Ser Gly Ile Arg Ile Ser Ser Val Phe Ala Ser Pro Ala Leu Arg Cys
            435                 440                 445

Val Gln Thr Ala Lys Leu Ile Leu Glu Glu Leu Lys Leu Glu Lys Lys
        450                 455                 460

Ile Lys Ile Arg Val Glu Pro Gly Ile Phe Glu Trp Thr Lys Trp Glu
465                 470                 475                 480

Ala Gly Lys Thr Thr Pro Thr Leu Met Ser Leu Glu Glu Leu Lys Glu
                485                 490                 495

Ala Asn Phe Asn Ile Asp Thr Asp Tyr Arg Pro Ala Phe Pro Leu Ser
            500                 505                 510

Ala Leu Met Pro Ala Glu Ser Tyr Gln Glu Tyr Met Asp Arg Cys Thr
        515                 520                 525

Ala Ser Met Val Gln Ile Val Asn Thr Cys Pro Gln Asp Thr Gly Val
    530                 535                 540

Ile Leu Ile Val Ser His Gly Ser Thr Leu Asp Ser Cys Thr Arg Pro
545                 550                 555                 560

Leu Leu Gly Leu Pro Arg Glu Cys Gly Asp Phe Ala Gln Leu Val
                565                 570                 575

Arg Lys Ile Pro Ser Leu Gly Met Cys Phe Cys Glu Glu Asn Lys Glu
            580                 585                 590

Glu Gly Lys Trp Glu Leu Val Asn Pro Pro Val Lys Thr Leu Thr His
        595                 600                 605

Gly Ala Asn Ala Ala Phe Asn Trp Arg Asn Trp Ile Ser Gly Asn
    610                 615                 620

<210> SEQ ID NO 3
<211> LENGTH: 120
<212> TYPE: DNA
<213> ORGANISM: Homo sapiens

<400> SEQUENCE: 3
agcccctcgc tcctggagcc cctcctggcc atgggcttcc cggtgcacac cgcgctgaaa      60
gcgttggcag ccacggggag gaagacggcg gaggaggcct tggcctggct gcatgatcat    120

<210> SEQ ID NO 4
<211> LENGTH: 40
<212> TYPE: PRT
<213> ORGANISM: Homo sapiens

<400> SEQUENCE: 4

Ser Pro Ser Leu Leu Glu Pro Leu Leu Ala Met Gly Phe Pro Val His
1               5                   10                  15

Thr Ala Leu Lys Ala Leu Ala Ala Thr Gly Arg Lys Thr Ala Glu Glu
                20                  25                  30

Ala Leu Ala Trp Leu His Asp His
            35                  40

<210> SEQ ID NO 5
<211> LENGTH: 1917
<212> TYPE: DNA
<213> ORGANISM: Homo sapiens

<400> SEQUENCE: 5
atggctgcga gagaggagct gtacagcaaa gtcacccccc ggaggaaccg ccaacagcgc      60
cccggcacca tcaagcatgg atcggcgctg acgtgctcc tctccatggg gttccccaga    120
```

```
gcccgcgcac aaaaagcctt ggcatccacg ggaggaagaa gtgttcaggc agcatgtgac      180
tggttattct cccatgtcgg tgacccct tc ctggatgacc ccctgccccg ggagtacgtc     240
ctctacctcc gtcccaccgg ccccttagca cagaagcttt ccgacttttg cagcagtcg      300
aagcagatct gcgggaagaa caaggcacac aacatcttcc cccacatcac actctgccag    360
ttctttatgt gcgaggacag caaggtggat gccctggggg aagccctgca gaccacggtc     420
agtcgctgga atgtaagtt ctcggccccg ctgcccctgg agtctatac gtcgtccaac       480
ttcatcggcc tctttgtaaa ggaagacagt gcggaggtcc tcaagaagtt tgctgctgac     540
tttgctgcag aggctgcatc caaaaccgaa gtgcatgtgg aacctcataa gaagcagcta     600
catgtgaccc tggcttacca cttccaagcc agccacctac ccaccctaga gaaactggcc     660
cagaacattg acgtcaagct agggtgtgac tgggtggcta ccatatttc tcgggatatc     720
cgatttgcta accatgagac attacaggtc atctacccct atccccaca aaatgacgat    780
gagctggagc tggtccccgg ggacttcatc ttcatgtctc caatggagca gaccagcacc    840
agcgagggtt ggatctatgg cacgtcctta accaccggct gctctggact cctgcctgag    900
aattacatta ccaaggctga tgaatgcagc acctggatat tcatggttc ttattcaatc     960
ttaaatacat cgtcatccaa ctctctcacg tttggggatg gagtattgga gaggcggcct   1020
tatgaggacc aggggctcgg ggagacgact cctcttacta tcatctgcca gcccatgcag   1080
ccgctgaggg tcaacagcca gcccggcccc cagaagcgat gccttttgt gtgtcggcat    1140
ggtgagagga tggatgttgt gtttgggaag tactggctgt cccagtgctt cgatgccaaa   1200
ggccgctaca tacgcaccaa cctgaacatg cctcatagtt tacctcagcg gagtggtggt    1260
ttccgagatt acgagaaaga tgctcccatc actgtgtttg gatgcatgca agcaagacta   1320
gtgggtgaag ccttattaga gagcaatacc attatcgatc atgtctattg ctccccgtcc   1380
cttcgctgcg ttcagactgc acacaatatc ttgaaaggtt tacaacaaga aaatcacttg   1440
aagatccgtg tagagcccgg cttatttgag tggacaaaat gggttgctgg gagcacatta   1500
cctgcatgga tacctccatc agagttagct gcagccaacc tgagtgttga tacaacctac   1560
agacctcaca ttccaatcag caaattagtt gtttcagaat cctatgatac ttatatcagt   1620
agaagtttcc aagtaacaaa agaaataata agtgaatgta aagtaaagg aaataacatc   1680
ctgattgtgg cccacgcatc ttcccttgaa gcgtgtacct gccaacttca gggcctgtca   1740
cctcagaact ccaaggactt cgtacaaatg gtccgaaaga tcccatatct gggattttgt   1800
tcctgtgaag aattaggaga aactggaata tggcagctga cagatccacc aatccttcct   1860
cttacccatg gaccaactgg gggcttcaac tggagagaga ccttgcttca agaataa     1917
```

<210> SEQ ID NO 6
<211> LENGTH: 638
<212> TYPE: PRT
<213> ORGANISM: Homo sapiens

<400> SEQUENCE: 6

Met Ala Ala Arg Glu Glu Leu Tyr Ser Lys Val Thr Pro Arg Arg Asn
1               5                   10                  15

Arg Gln Gln Arg Pro Gly Thr Ile Lys His Gly Ser Ala Leu Asp Val
            20                  25                  30

Leu Leu Ser Met Gly Phe Pro Arg Ala Arg Ala Gln Lys Ala Leu Ala
        35                  40                  45

Ser Thr Gly Gly Arg Ser Val Gln Ala Ala Cys Asp Trp Leu Phe Ser
    50                  55                  60

-continued

```
His Val Gly Asp Pro Phe Leu Asp Pro Leu Pro Arg Glu Tyr Val
 65                  70                  75                  80

Leu Tyr Leu Arg Pro Thr Gly Pro Leu Ala Gln Lys Leu Ser Asp Phe
                 85                  90                  95

Trp Gln Gln Ser Lys Gln Ile Cys Gly Lys Asn Lys Ala His Asn Ile
                100                 105                 110

Phe Pro His Ile Thr Leu Cys Gln Phe Phe Met Cys Glu Asp Ser Lys
                115                 120                 125

Val Asp Ala Leu Gly Glu Ala Leu Gln Thr Thr Val Ser Arg Trp Lys
130                 135                 140

Cys Lys Phe Ser Ala Pro Leu Pro Leu Glu Leu Tyr Thr Ser Ser Asn
145                 150                 155                 160

Phe Ile Gly Leu Phe Val Lys Glu Asp Ser Ala Glu Val Leu Lys Lys
                165                 170                 175

Phe Ala Ala Asp Phe Ala Ala Glu Ala Ala Ser Lys Thr Glu Val His
                180                 185                 190

Val Glu Pro His Lys Lys Gln Leu His Val Thr Leu Ala Tyr His Phe
                195                 200                 205

Gln Ala Ser His Leu Pro Thr Leu Glu Lys Leu Ala Gln Asn Ile Asp
210                 215                 220

Val Lys Leu Gly Cys Asp Trp Val Ala Thr Ile Phe Ser Arg Asp Ile
225                 230                 235                 240

Arg Phe Ala Asn His Glu Thr Leu Gln Val Ile Tyr Pro Tyr Thr Pro
                245                 250                 255

Gln Asn Asp Asp Glu Leu Glu Leu Val Pro Gly Asp Phe Ile Phe Met
                260                 265                 270

Ser Pro Met Glu Gln Thr Ser Thr Ser Glu Gly Trp Ile Tyr Gly Thr
                275                 280                 285

Ser Leu Thr Thr Gly Cys Ser Gly Leu Leu Pro Glu Asn Tyr Ile Thr
                290                 295                 300

Lys Ala Asp Glu Cys Ser Thr Trp Ile Phe His Gly Ser Tyr Ser Ile
305                 310                 315                 320

Leu Asn Thr Ser Ser Asn Ser Leu Thr Phe Gly Asp Gly Val Leu
                325                 330                 335

Glu Arg Arg Pro Tyr Glu Asp Gln Gly Leu Gly Glu Thr Thr Pro Leu
                340                 345                 350

Thr Ile Ile Cys Gln Pro Met Gln Pro Leu Arg Val Asn Ser Gln Pro
                355                 360                 365

Gly Pro Gln Lys Arg Cys Leu Phe Val Cys Arg His Gly Glu Arg Met
                370                 375                 380

Asp Val Val Phe Gly Lys Tyr Trp Leu Ser Gln Cys Phe Asp Ala Lys
385                 390                 395                 400

Gly Arg Tyr Ile Arg Thr Asn Leu Asn Met Pro His Ser Leu Pro Gln
                405                 410                 415

Arg Ser Gly Gly Phe Arg Asp Tyr Glu Lys Asp Ala Pro Ile Thr Val
                420                 425                 430

Phe Gly Cys Met Gln Ala Arg Leu Val Gly Glu Ala Leu Leu Glu Ser
                435                 440                 445

Asn Thr Ile Ile Asp His Val Tyr Cys Ser Pro Ser Leu Arg Cys Val
                450                 455                 460

Gln Thr Ala His Asn Ile Leu Lys Gly Leu Gln Gln Glu Asn His Leu
465                 470                 475                 480

Lys Ile Arg Val Glu Pro Gly Leu Phe Glu Trp Thr Lys Trp Val Ala
                485                 490                 495
```

```
Gly Ser Thr Leu Pro Ala Trp Ile Pro Pro Ser Glu Leu Ala Ala Ala
                500                 505                 510

Asn Leu Ser Val Asp Thr Thr Tyr Arg Pro His Ile Pro Ile Ser Lys
            515                 520                 525

Leu Val Val Ser Glu Ser Tyr Asp Thr Tyr Ile Ser Arg Ser Phe Gln
        530                 535                 540

Val Thr Lys Glu Ile Ile Ser Glu Cys Lys Ser Lys Gly Asn Asn Ile
545                 550                 555                 560

Leu Ile Val Ala His Ala Ser Ser Leu Glu Ala Cys Thr Cys Gln Leu
                565                 570                 575

Gln Gly Leu Ser Pro Gln Asn Ser Lys Asp Phe Val Gln Met Val Arg
            580                 585                 590

Lys Ile Pro Tyr Leu Gly Phe Cys Ser Cys Glu Glu Leu Gly Glu Thr
        595                 600                 605

Gly Ile Trp Gln Leu Thr Asp Pro Pro Ile Leu Pro Leu Thr His Gly
610                 615                 620

Pro Thr Gly Gly Phe Asn Trp Arg Glu Thr Leu Leu Gln Glu
625                 630                 635

<210> SEQ ID NO 7
<211> LENGTH: 138
<212> TYPE: DNA
<213> ORGANISM: Homo sapiens

<400> SEQUENCE: 7
cgccccggca ccatcaagca tggatcggcg ctggacgtgc tcctctccat ggggttcccc      60
agagcccgcg cacaaaaagc cttggcatcc acgggaggaa gaagtgttca ggcagcatgt     120
gactggttat tctcccat                                                   138

<210> SEQ ID NO 8
<211> LENGTH: 46
<212> TYPE: PRT
<213> ORGANISM: Homo sapiens

<400> SEQUENCE: 8

Arg Pro Gly Thr Ile Lys His Gly Ser Ala Leu Asp Val Leu Leu Ser
1               5                   10                  15

Met Gly Phe Pro Arg Ala Arg Ala Gln Lys Ala Leu Ala Ser Thr Gly
            20                  25                  30

Gly Arg Ser Val Gln Ala Ala Cys Asp Trp Leu Phe Ser His
        35                  40                  45

<210> SEQ ID NO 9
<211> LENGTH: 13
<212> TYPE: PRT
<213> ORGANISM: Homo sapiens

<400> SEQUENCE: 9

Met Tyr Thr Phe Ser Lys Ala Thr Asp Lys His Ser Arg
1               5                   10

<210> SEQ ID NO 10
<211> LENGTH: 12
<212> TYPE: PRT
<213> ORGANISM: Homo sapiens

<400> SEQUENCE: 10

Ile Ala Gly Asp Ala Leu Leu Asp Ser Gly Ile Arg
1               5                   10
```

```
<210> SEQ ID NO 11
<211> LENGTH: 7
<212> TYPE: PRT
<213> ORGANISM: Homo sapiens

<400> SEQUENCE: 11

Thr Leu Glu Gln Leu Ala Arg
1               5

<210> SEQ ID NO 12
<211> LENGTH: 7
<212> TYPE: PRT
<213> ORGANISM: Homo sapiens

<400> SEQUENCE: 12

Val Asp Gln Ile Phe Gly Lys
1               5

<210> SEQ ID NO 13
<211> LENGTH: 18
<212> TYPE: DNA
<213> ORGANISM: Artificial
<220> FEATURE:
<223> OTHER INFORMATION: Oligonucleotide Primer

<400> SEQUENCE: 13
ggcaggaaga gatggcag                                                 18

<210> SEQ ID NO 14
<211> LENGTH: 24
<212> TYPE: DNA
<213> ORGANISM: Artificial
<220> FEATURE:
<223> OTHER INFORMATION: Oligonucleotide Primer

<400> SEQUENCE: 14
gaggttatga caacatcacc gtgg                                          24

<210> SEQ ID NO 15
<211> LENGTH: 32
<212> TYPE: DNA
<213> ORGANISM: Artificial
<220> FEATURE:
<223> OTHER INFORMATION: Oligonucleotide Primer

<400> SEQUENCE: 15
tgcaatgacc cttccctaga cgacatcccc ca                                 32

<210> SEQ ID NO 16
<211> LENGTH: 35
<212> TYPE: DNA
<213> ORGANISM: Artificial
<220> FEATURE:
<223> OTHER INFORMATION: Oligonucleotide Primer

<400> SEQUENCE: 16
gcggctcttg agcttgttgg agaccttggc gtaga                              35

<210> SEQ ID NO 17
<211> LENGTH: 25
<212> TYPE: DNA
<213> ORGANISM: Artificial
<220> FEATURE:
<223> OTHER INFORMATION: Oligonucleotide Primer

<400> SEQUENCE: 17
tcacagcgga cgggctgccg gggct                                         25
```

```
<210> SEQ ID NO 18
<211> LENGTH: 31
<212> TYPE: DNA
<213> ORGANISM: Artificial
<220> FEATURE:
<223> OTHER INFORMATION: Oligonucleotide Primer

<400> SEQUENCE: 18
gatcccaatc accaggccct cgctggtggt c                                    31

<210> SEQ ID NO 19
<211> LENGTH: 649
<212> TYPE: PRT
<213> ORGANISM: Homo sapiens

<400> SEQUENCE: 19
```

| | | | | | | | | | | | | | | |
|---|---|---|---|---|---|---|---|---|---|---|---|---|---|---|
| Met | Ala | Gln | Tyr | Gly | His | Pro | Ser | Pro | Leu | Gly | Met | Ala | Arg | Glu |
| 1 | | | | 5 | | | | | 10 | | | | | 15 |
| Glu | Leu | Tyr | Ser | Lys | Val | Thr | Pro | Arg | Arg | Asn | Arg | Gln | Gln | Arg | Pro |
| | | | 20 | | | | | 25 | | | | | 30 | | |
| Gly | Thr | Ile | Lys | His | Gly | Ser | Ala | Leu | Asp | Val | Leu | Leu | Ser | Met | Gly |
| | | | 35 | | | | | 40 | | | | | 45 | | |
| Phe | Pro | Arg | Ala | Arg | Ala | Gln | Lys | Ala | Leu | Ala | Ser | Thr | Gly | Gly | Arg |
| 50 | | | | | 55 | | | | | 60 | | | | | |
| Ser | Val | Gln | Ala | Ala | Cys | Asp | Trp | Leu | Phe | Ser | His | Val | Gly | Asp | Pro |
| 65 | | | | | 70 | | | | | 75 | | | | | 80 |
| Phe | Leu | Asp | Asp | Pro | Leu | Pro | Arg | Glu | Tyr | Val | Leu | Tyr | Leu | Arg | Pro |
| | | | | 85 | | | | | 90 | | | | | 95 | |
| Thr | Gly | Pro | Leu | Ala | Gln | Lys | Leu | Ser | Asp | Phe | Trp | Gln | Gln | Ser | Lys |
| | | | 100 | | | | | 105 | | | | | 110 | | |
| Gln | Ile | Cys | Gly | Lys | Asn | Lys | Ala | His | Asn | Ile | Phe | Pro | His | Ile | Thr |
| | | | 115 | | | | | 120 | | | | | 125 | | |
| Leu | Cys | Gln | Phe | Phe | Met | Cys | Glu | Asp | Ser | Lys | Val | Asp | Ala | Leu | Gly |
| 130 | | | | | 135 | | | | | 140 | | | | | |
| Glu | Ala | Leu | Gln | Thr | Thr | Val | Ser | Arg | Trp | Lys | Cys | Lys | Phe | Ser | Ala |
| 145 | | | | | 150 | | | | | 155 | | | | | 160 |
| Pro | Leu | Pro | Leu | Glu | Leu | Tyr | Thr | Ser | Ser | Asn | Phe | Ile | Gly | Leu | Phe |
| | | | | 165 | | | | | 170 | | | | | 175 | |
| Val | Lys | Glu | Asp | Ser | Ala | Glu | Val | Leu | Lys | Lys | Phe | Ala | Ala | Asp | Phe |
| | | | 180 | | | | | 185 | | | | | 190 | | |
| Ala | Ala | Glu | Ala | Ala | Ser | Lys | Thr | Glu | Val | His | Val | Glu | Pro | His | Lys |
| | | | 195 | | | | | 200 | | | | | 205 | | |
| Lys | Gln | Leu | His | Val | Thr | Leu | Ala | Tyr | His | Phe | Gln | Ala | Ser | His | Leu |
| 210 | | | | | 215 | | | | | 220 | | | | | |
| Pro | Thr | Leu | Glu | Lys | Leu | Ala | Gln | Asn | Ile | Asp | Val | Lys | Leu | Gly | Cys |
| 225 | | | | | 230 | | | | | 235 | | | | | 240 |
| Asp | Trp | Val | Ala | Thr | Ile | Phe | Ser | Arg | Asp | Ile | Arg | Phe | Ala | Asn | His |
| | | | | 245 | | | | | 250 | | | | | 255 | |
| Glu | Thr | Leu | Gln | Val | Ile | Tyr | Pro | Tyr | Thr | Pro | Gln | Asn | Asp | Asp | Glu |
| | | | 260 | | | | | 265 | | | | | 270 | | |
| Leu | Glu | Leu | Val | Pro | Gly | Asp | Phe | Ile | Phe | Met | Ser | Pro | Met | Glu | Gln |
| | | | 275 | | | | | 280 | | | | | 285 | | |
| Thr | Ser | Thr | Ser | Glu | Gly | Trp | Ile | Tyr | Gly | Thr | Ser | Leu | Thr | Thr | Gly |
| | | | 290 | | | | | 295 | | | | | 300 | | |
| Cys | Ser | Gly | Leu | Leu | Pro | Glu | Asn | Tyr | Ile | Thr | Lys | Ala | Asp | Glu | Cys |
| 305 | | | | | 310 | | | | | 315 | | | | | 320 |

-continued

```
Ser Thr Trp Ile Phe His Gly Ser Tyr Ser Ile Leu Asn Thr Ser Ser
                325                 330                 335

Ser Asn Ser Leu Thr Phe Gly Asp Gly Val Leu Glu Arg Arg Pro Tyr
            340                 345                 350

Glu Asp Gln Gly Leu Gly Glu Thr Thr Pro Leu Thr Ile Ile Cys Gln
        355                 360                 365

Pro Met Gln Pro Leu Arg Val Asn Ser Gln Pro Gly Pro Gln Lys Arg
    370                 375                 380

Cys Leu Phe Val Cys Arg His Gly Glu Arg Met Asp Val Val Phe Gly
385                 390                 395                 400

Lys Tyr Trp Leu Ser Gln Cys Phe Asp Ala Lys Gly Arg Tyr Ile Arg
                405                 410                 415

Thr Asn Leu Asn Met Pro His Ser Leu Pro Gln Arg Ser Gly Gly Phe
            420                 425                 430

Arg Asp Tyr Glu Lys Asp Ala Pro Ile Thr Val Phe Gly Cys Met Gln
        435                 440                 445

Ala Arg Leu Val Gly Glu Ala Leu Leu Glu Ser Asn Thr Ile Ile Asp
    450                 455                 460

His Val Tyr Cys Ser Pro Ser Leu Arg Cys Val Gln Thr Ala His Asn
465                 470                 475                 480

Ile Leu Lys Gly Leu Gln Gln Glu Asn His Leu Lys Ile Arg Val Glu
                485                 490                 495

Pro Gly Leu Phe Glu Trp Thr Lys Trp Val Ala Gly Ser Thr Leu Pro
            500                 505                 510

Ala Trp Ile Pro Pro Ser Glu Leu Ala Ala Ala Asn Leu Ser Val Asp
        515                 520                 525

Thr Thr Tyr Arg Pro His Ile Pro Ile Ser Lys Leu Val Val Ser Glu
    530                 535                 540

Ser Tyr Asp Thr Tyr Ile Ser Arg Ser Phe Gln Val Thr Lys Glu Ile
545                 550                 555                 560

Ile Ser Glu Cys Lys Ser Lys Gly Asn Asn Ile Leu Ile Val Ala His
                565                 570                 575

Ala Ser Ser Leu Glu Ala Cys Thr Cys Gln Leu Gln Gly Leu Ser Pro
            580                 585                 590

Gln Asn Ser Lys Asp Phe Val Gln Met Val Arg Lys Ile Pro Tyr Leu
        595                 600                 605

Gly Phe Cys Ser Cys Glu Glu Leu Gly Glu Thr Gly Ile Trp Gln Leu
    610                 615                 620

Thr Asp Pro Pro Ile Leu Pro Leu Thr His Gly Pro Thr Gly Gly Phe
625                 630                 635                 640

Asn Trp Arg Glu Thr Leu Leu Gln Glu
                645
```